United States Patent
Chanduszko

(10) Patent No.: US 10,588,765 B2
(45) Date of Patent: Mar. 17, 2020

(54) UNIFORMLY EXPANDABLE STENT

(71) Applicant: C.R. Bard, Inc., Murray Hills, NJ (US)

(72) Inventor: Andrzej J. Chanduszko, Chandler, AZ (US)

(73) Assignee: C. R. Bard, Inc., Franklin Lakes, NJ (US)

(*) Notice: Subject to any disclaimer, the term of this patent is extended or adjusted under 35 U.S.C. 154(b) by 203 days.

(21) Appl. No.: 14/754,614

(22) Filed: Jun. 29, 2015

(65) Prior Publication Data

US 2015/0297376 A1    Oct. 22, 2015

Related U.S. Application Data

(62) Division of application No. 13/797,747, filed on Mar. 12, 2013, now Pat. No. 9,066,825.

(Continued)

(51) Int. Cl.
*A61F 2/915* (2013.01)
*A61F 2/90* (2013.01)
(Continued)

(52) U.S. Cl.
CPC ............... *A61F 2/915* (2013.01); *A61F 2/90* (2013.01); *A61F 2002/072* (2013.01);
(Continued)

(58) Field of Classification Search
CPC .... A61F 2/915; A61F 2/90; A61F 2002/9155; A61F 2002/91533; A61F 2002/825;
(Continued)

(56) References Cited

U.S. PATENT DOCUMENTS 4,501,264 A    2/1985  Rockey
4,641,653 A    2/1987  Rockey
(Continued)

FOREIGN PATENT DOCUMENTS

DE    29701758 U1    3/1997
DE    29702671 U1    4/1997
(Continued)

OTHER PUBLICATIONS

PCT/US13/30598 filed Mar. 12, 2013 International Search Report and Written Opinion dated Jul. 22, 2013.
(Continued)

*Primary Examiner* — Richard G Louis
(74) *Attorney, Agent, or Firm* — Rutan & Tucker LLP

(57) ABSTRACT

An intraluminal prosthesis includes a stent architecture having a series of stent elements repeating along a circumferential axis. One series of stent elements includes v-shaped stent elements having at least four different orientations, and V-shaped stent elements connecting adjacent v-shaped stent elements. One series of stent elements includes R-shaped stent elements having at least four different orientations, and U-shaped stent elements having at least two different orientations, the U-shaped stent elements connecting adjacent R-shaped stent elements. Adjacent series of stent elements can be connected by connectors. Portions of the stent elements may narrow in width along a length thereof. The stent architecture may include radiopaque element receiving members. The stent architecture may be formed by machining a metal or polymer tube. The intraluminal prosthesis may include one or more graft layers.

9 Claims, 27 Drawing Sheets

Related U.S. Application Data

(60) Provisional application No. 61/646,806, filed on May 14, 2012, provisional application No. 61/678,485, filed on Aug. 1, 2012, provisional application No. 61/708,445, filed on Oct. 1, 2012.

(51) Int. Cl.
*A61F 2/07* (2013.01)
*A61F 2/82* (2013.01)

(52) U.S. Cl.
CPC . *A61F 2002/825* (2013.01); *A61F 2002/9155* (2013.01); *A61F 2002/91533* (2013.01); *A61F 2002/91575* (2013.01); *A61F 2210/0076* (2013.01); *A61F 2230/0054* (2013.01); *A61F 2250/0036* (2013.01); *F04C 2270/041* (2013.01)

(58) Field of Classification Search
CPC ...... A61F 2210/0076; A61F 2230/0054; A61F 2250/0036; A61F 2002/91575; A61F 2002/072; F04C 2270/041
See application file for complete search history.

(56) References Cited

U.S. PATENT DOCUMENTS

| | | |
|---|---|---|
| 4,733,665 A | 3/1988 | Palmaz |
| 4,739,762 A | 4/1988 | Palmaz |
| 4,740,207 A | 4/1988 | Kreamer |
| 4,763,653 A | 8/1988 | Rockey |
| 4,776,337 A | 10/1988 | Palmaz |
| 4,886,062 A | 12/1989 | Wiktor |
| 5,035,706 A | 7/1991 | Giantureo et al. |
| 5,059,211 A | 10/1991 | Stack et al. |
| 5,067,957 A | 11/1991 | Jervis |
| 5,102,403 A | 4/1992 | Alt |
| 5,102,417 A | 4/1992 | Palmaz |
| 5,135,536 A | 8/1992 | Hillstead |
| 5,190,546 A | 3/1993 | Jervis |
| 5,195,984 A | 3/1993 | Schatz |
| 5,292,331 A | 3/1994 | Boneau |
| 5,356,423 A | 10/1994 | Tihon et al. |
| 5,366,504 A | 11/1994 | Andersen et al. |
| 5,411,552 A | 5/1995 | Andersen et al. |
| 5,415,664 A | 5/1995 | Pinchuk |
| 5,421,955 A | 6/1995 | Lau et al. |
| 5,423,851 A | 6/1995 | Samuels |
| 5,445,625 A | 8/1995 | Voda |
| 5,449,373 A | 9/1995 | Pinchasik et al. |
| 5,451,233 A | 9/1995 | Yock |
| 5,514,154 A | 5/1996 | Lau et al. |
| 5,516,781 A | 5/1996 | Morris et al. |
| 5,563,146 A | 10/1996 | Morris et al. |
| 5,593,442 A | 1/1997 | Klein |
| 5,603,721 A | 2/1997 | Lau et al. |
| 5,609,627 A | 3/1997 | Goicoechea et al. |
| 5,630,829 A | 5/1997 | Lauterjung |
| 5,632,772 A | 5/1997 | Alcime et al. |
| 5,639,278 A | 6/1997 | Dereume et al. |
| 5,643,312 A | 7/1997 | Fischell et al. |
| 5,645,559 A | 7/1997 | Hachtman et al. |
| 5,653,727 A | 8/1997 | Wiktor |
| 5,653,760 A | 8/1997 | Saffran |
| 5,674,278 A | 10/1997 | Boneau |
| 5,683,450 A | 11/1997 | Goicoechea et al. |
| 5,693,086 A | 12/1997 | Goicoechea et al. |
| 5,695,516 A | 12/1997 | Fischell et al. |
| 5,697,971 A | 12/1997 | Fischell et al. |
| 5,707,386 A | 1/1998 | Schnepp-Pesch et al. |
| 5,716,365 A | 2/1998 | Goicoechea et al. |
| 5,718,159 A | 2/1998 | Thompson |
| 5,718,724 A | 2/1998 | Goicoechea et al. |
| 5,723,004 A | 3/1998 | Dereume et al. |
| 5,725,548 A | 3/1998 | Jayaraman |
| 5,728,158 A | 3/1998 | Lau et al. |
| 5,733,303 A | 3/1998 | Israel et al. |
| 5,735,893 A | 4/1998 | Lau et al. |
| 5,749,880 A | 5/1998 | Banas et al. |
| 5,755,776 A | 5/1998 | Ai-Saadon |
| 5,755,777 A | 5/1998 | Chuter |
| 5,758,562 A | 6/1998 | Thompson |
| 5,766,238 A | 6/1998 | Lau et al. |
| 5,776,180 A | 7/1998 | Goicoechea et al. |
| 5,777,004 A | 7/1998 | Trautman |
| 5,788,626 A | 8/1998 | Thompson |
| 5,800,508 A | 9/1998 | Goicoechea et al. |
| 5,807,404 A | 9/1998 | Richter |
| 5,810,870 A | 9/1998 | Myers et al. |
| 5,817,126 A | 10/1998 | Imran |
| 5,824,059 A | 10/1998 | Wijay |
| 5,843,120 A | 12/1998 | Israel et al. |
| 5,843,175 A | 12/1998 | Frantzen |
| 5,855,598 A | 1/1999 | Pinchuk |
| 5,868,782 A | 2/1999 | Frantzen |
| 5,876,448 A | 3/1999 | Thompson et al. |
| 5,876,449 A | 3/1999 | Starck et al. |
| 5,879,370 A | 3/1999 | Fischell et al. |
| 5,879,382 A | 3/1999 | Boneau |
| 5,895,406 A | 4/1999 | Gray et al. |
| 5,902,317 A | 5/1999 | Kleshinski et al. |
| 5,906,641 A | 5/1999 | Thompson et al. |
| 5,913,897 A | 6/1999 | Corso, Jr. et al. |
| 5,916,263 A | 6/1999 | Goicoechea et al. |
| 5,919,224 A | 7/1999 | Thompson et al. |
| 5,922,020 A | 7/1999 | Klein et al. |
| 5,922,021 A | 7/1999 | Jang |
| 5,925,061 A | 7/1999 | Ogi et al. |
| 5,931,866 A | 8/1999 | Frantzen |
| 5,935,162 A | 8/1999 | Dang |
| 5,938,682 A | 8/1999 | Hojeibane et al. |
| 5,938,696 A | 8/1999 | Goicoechea et al. |
| 5,948,018 A | 9/1999 | Dereume et al. |
| 5,957,974 A | 9/1999 | Thompson et al. |
| 5,964,798 A | 10/1999 | Imran |
| 5,972,018 A | 10/1999 | Israel et al. |
| 5,980,553 A | 11/1999 | Gray et al. |
| 6,007,575 A | 12/1999 | Samuels |
| 6,013,091 A | 1/2000 | Ley et al. |
| 6,019,786 A | 2/2000 | Thompson |
| 6,019,787 A | 2/2000 | Richard et al. |
| 6,019,789 A | 2/2000 | Dinh et al. |
| 6,042,606 A | 3/2000 | Frantzen |
| 6,051,020 A | 4/2000 | Goicoechea et al. |
| 6,056,776 A | 5/2000 | Lau et al. |
| 6,066,167 A | 5/2000 | Lau et al. |
| 6,066,168 A | 5/2000 | Lau et al. |
| 6,066,169 A | 5/2000 | McGuinness |
| 6,083,213 A | 7/2000 | Voda |
| 6,117,165 A | 9/2000 | Becker |
| 6,117,167 A | 9/2000 | Goicoechea et al. |
| 6,120,536 A | 9/2000 | Ding et al. |
| 6,129,754 A | 10/2000 | Kanesaka et al. |
| 6,129,755 A | 10/2000 | Mathis et al. |
| 6,132,460 A | 10/2000 | Thompson |
| 6,132,461 A | 10/2000 | Thompson |
| 6,146,403 A | 11/2000 | St. Germain |
| 6,152,946 A | 11/2000 | Broome et al. |
| 6,159,156 A | 12/2000 | Van Bockel |
| 6,162,243 A | 12/2000 | Gray et al. |
| 6,165,210 A | 12/2000 | Lau et al. |
| 6,165,211 A | 12/2000 | Thompson |
| 6,165,212 A | 12/2000 | Dereume et al. |
| 6,165,213 A | 12/2000 | Goicoechea et al. |
| 6,168,614 B1 | 1/2001 | Andersen et al. |
| 6,190,358 B1 | 2/2001 | Fitzmaurice et al. |
| 6,190,403 B1 | 2/2001 | Fischell et al. |
| 6,190,406 B1 | 2/2001 | Duerig et al. |
| 6,193,747 B1 | 2/2001 | von Oepen |
| 6,193,748 B1 | 2/2001 | Thompson et al. |
| 6,231,598 B1 | 5/2001 | Berry et al. |
| 6,231,599 B1 | 5/2001 | Ley |
| 6,245,100 B1 | 6/2001 | Davila et al. |
| 6,254,631 B1 | 7/2001 | Thompson |

(56) References Cited

U.S. PATENT DOCUMENTS

| | | |
|---|---|---|
| 6,280,466 B1 | 8/2001 | Kugler et al. |
| 6,293,966 B1 | 9/2001 | Frantzen |
| 6,299,635 B1 | 10/2001 | Frantzen |
| 6,302,906 B1 | 10/2001 | Goicoechea et al. |
| 6,306,141 B1 | 10/2001 | Jervis |
| 6,309,412 B1 | 10/2001 | Lau et al. |
| 6,309,414 B1 | 10/2001 | Rolando et al. |
| 6,325,821 B1 | 12/2001 | Gaschino et al. |
| 6,325,826 B1 | 12/2001 | Vardi et al. |
| 6,331,189 B1 * | 12/2001 | Wolinsky ............... A61F 2/91 623/1.15 |
| 6,334,870 B1 | 1/2002 | Ehr et al. |
| 6,342,067 B1 | 1/2002 | Mathis et al. |
| 6,342,068 B1 | 1/2002 | Thompson |
| 6,344,053 B1 | 2/2002 | Boneau |
| 6,348,065 B1 | 2/2002 | Brown et al. |
| 6,358,274 B1 | 3/2002 | Thompson |
| 6,395,020 B1 | 5/2002 | Ley et al. |
| 6,423,090 B1 | 7/2002 | Hancock |
| 6,423,091 B1 | 7/2002 | Hojeibane |
| 6,432,133 B1 | 8/2002 | Lau et al. |
| 6,443,982 B1 | 9/2002 | Israel et al. |
| 6,464,722 B2 | 10/2002 | Israel et al. |
| 6,475,195 B1 | 11/2002 | Voda |
| 6,475,233 B2 | 11/2002 | Trozera |
| 6,485,509 B2 | 11/2002 | Killion et al. |
| 6,485,511 B2 | 11/2002 | Lau et al. |
| 6,488,694 B1 | 12/2002 | Lau et al. |
| 6,491,718 B1 | 12/2002 | Ahmad |
| 6,511,504 B1 | 1/2003 | Lau et al. |
| 6,511,505 B2 | 1/2003 | Cox et al. |
| 6,517,572 B2 | 2/2003 | Kugler et al. |
| 6,520,985 B1 | 2/2003 | Burpee et al. |
| 6,524,334 B1 | 2/2003 | Thompson |
| 6,527,789 B1 | 3/2003 | Lau et al. |
| 6,533,807 B2 | 3/2003 | Wolinsky et al. |
| 6,533,808 B1 | 3/2003 | Thompson |
| 6,533,809 B2 | 3/2003 | von Oepen |
| 6,540,774 B1 | 4/2003 | Cox |
| 6,540,775 B1 | 4/2003 | Fischell et al. |
| 6,558,415 B2 | 5/2003 | Thompson |
| 6,565,602 B2 | 5/2003 | Rolando et al. |
| 6,572,649 B2 | 6/2003 | Berry et al. |
| 6,579,310 B1 | 6/2003 | Cox et al. |
| 6,582,458 B1 | 6/2003 | White et al. |
| 6,582,462 B1 | 6/2003 | Andersen et al. |
| 6,585,764 B2 | 7/2003 | Wright et al. |
| 6,596,021 B1 | 7/2003 | Lootz |
| 6,596,022 B2 | 7/2003 | Lau et al. |
| 6,602,284 B2 | 8/2003 | Cox et al. |
| 6,605,057 B2 | 8/2003 | Fitzmaurice et al. |
| 6,613,073 B1 | 9/2003 | White et al. |
| 6,613,080 B1 | 9/2003 | Lootz |
| 6,616,690 B2 | 9/2003 | Rolando et al. |
| 6,620,193 B1 | 9/2003 | Lau et al. |
| 6,626,933 B1 | 9/2003 | Lau et al. |
| 6,629,991 B1 | 10/2003 | Lau et al. |
| 6,629,994 B2 | 10/2003 | Gomez et al. |
| 6,656,219 B1 | 12/2003 | Wiktor |
| 6,656,220 B1 | 12/2003 | Gomez et al. |
| 6,663,652 B2 | 12/2003 | Daniel et al. |
| 6,679,910 B1 | 1/2004 | Granada |
| 6,689,159 B2 | 2/2004 | Lau et al. |
| 6,699,277 B1 | 3/2004 | Freidberg et al. |
| 6,699,281 B2 | 3/2004 | Vallana et al. |
| 6,706,061 B1 | 3/2004 | Fischell et al. |
| 6,730,116 B1 | 5/2004 | Wolinsky et al. |
| 6,743,180 B1 | 6/2004 | Van Bockel |
| 6,743,252 B1 | 6/2004 | Bates et al. |
| 6,746,477 B2 * | 6/2004 | Moore ............... A61F 2/91 623/1.1 |
| 6,746,773 B2 | 6/2004 | Llanos et al. |
| 6,773,455 B2 | 8/2004 | Allen et al. |
| 6,776,796 B2 | 8/2004 | Falotico et al. |
| 6,796,999 B2 | 9/2004 | Pinchasik |
| 6,808,536 B2 | 10/2004 | Wright et al. |
| 6,811,566 B1 | 11/2004 | Penn et al. |
| 6,821,292 B2 | 11/2004 | Pazienza et al. |
| 6,827,732 B2 | 12/2004 | Thompson |
| 6,858,037 B2 | 2/2005 | Penn et al. |
| 6,860,900 B2 | 3/2005 | Clerc et al. |
| 6,863,685 B2 | 3/2005 | Davila et al. |
| 6,866,679 B2 | 3/2005 | Kusleika |
| 6,881,222 B2 | 4/2005 | White et al. |
| 6,881,223 B2 | 4/2005 | Penn et al. |
| 6,884,260 B2 | 4/2005 | Kugler et al. |
| 6,896,696 B2 | 5/2005 | Doran et al. |
| 6,896,698 B2 | 5/2005 | Rolando et al. |
| 6,908,479 B2 | 6/2005 | Lau et al. |
| 6,923,828 B1 | 8/2005 | Wiktor |
| 6,929,660 B1 | 8/2005 | Ainsworth et al. |
| 6,974,475 B1 | 12/2005 | Wall |
| 6,976,993 B2 | 12/2005 | Schaldach et al. |
| 7,004,968 B2 | 2/2006 | Lootz et al. |
| 7,037,330 B1 | 5/2006 | Rivelli, Jr. et al. |
| 7,060,091 B2 | 6/2006 | Killion et al. |
| 7,070,614 B1 | 7/2006 | Neuss et al. |
| 7,081,130 B2 | 7/2006 | Jang |
| 7,094,255 B2 | 8/2006 | Penn et al. |
| 7,108,714 B1 | 9/2006 | Becker |
| 7,122,049 B2 | 10/2006 | Banas et al. |
| 7,128,753 B1 | 10/2006 | Bonutti et al. |
| 7,135,039 B2 | 11/2006 | De Scheerder et al. |
| 7,172,623 B2 | 2/2007 | Hansen et al. |
| 7,204,848 B1 | 4/2007 | Brown et al. |
| 7,211,109 B2 | 5/2007 | Thompson |
| 7,217,286 B2 | 5/2007 | Falotico et al. |
| 7,217,290 B2 | 5/2007 | Bonutti |
| 7,223,283 B2 | 5/2007 | Chouinard |
| 7,223,286 B2 | 5/2007 | Wright et al. |
| 7,229,473 B2 | 6/2007 | Falotico et al. |
| 7,240,516 B2 | 7/2007 | Pryor |
| 7,252,679 B2 | 8/2007 | Fischell et al. |
| 7,267,684 B2 | 9/2007 | Rolando et al. |
| 7,279,004 B2 | 10/2007 | Shanley |
| 7,300,662 B2 | 11/2007 | Falotico et al. |
| 7,320,702 B2 | 1/2008 | Harnmersmark et al. |
| 7,323,189 B2 | 1/2008 | Pathak |
| 7,329,277 B2 | 2/2008 | Addonizio et al. |
| D568,476 S | 5/2008 | Cottone, Jr. et al. |
| D569,976 S | 5/2008 | Raj D et al. |
| 7,384,427 B2 | 6/2008 | Tanaka et al. |
| 7,404,823 B2 * | 7/2008 | Gregorich ............... A61F 2/91 623/1.15 |
| D581,054 S | 11/2008 | Moore |
| 7,479,158 B2 | 1/2009 | Gregorich |
| 7,491,228 B2 | 2/2009 | Doran et al. |
| 7,527,644 B2 | 5/2009 | Mangiardi et al. |
| 7,537,609 B2 | 5/2009 | Davidson et al. |
| D597,671 S | 8/2009 | Cottone, Jr. et al. |
| 7,591,844 B2 | 9/2009 | Llanos et al. |
| 7,611,531 B2 | 11/2009 | Calisse |
| 7,622,135 B2 | 11/2009 | Pathak et al. |
| 7,632,300 B2 | 12/2009 | Thompson |
| 7,632,302 B2 | 12/2009 | Vreeman et al. |
| 7,682,384 B2 | 3/2010 | Addonizio et al. |
| 7,722,661 B2 | 5/2010 | Lenz et al. |
| 7,731,744 B1 | 6/2010 | Cox |
| 7,744,641 B2 | 6/2010 | Leynov et al. |
| 7,753,948 B2 | 7/2010 | Roeder et al. |
| 7,763,064 B2 | 7/2010 | Pinchasik |
| D622,387 S | 8/2010 | Igaki |
| D622,388 S | 8/2010 | Igaki |
| 7,766,956 B2 | 8/2010 | Jang |
| 7,766,957 B2 | 8/2010 | Moriuchi |
| 7,803,180 B2 | 9/2010 | Burpee et al. |
| 7,806,918 B2 | 10/2010 | Nissl et al. |
| 7,815,675 B2 | 10/2010 | Davidson et al. |
| 7,829,111 B2 | 11/2010 | Pathak |
| 7,842,080 B2 | 11/2010 | Chouinard |
| D635,261 S | 3/2011 | Rossi |
| D635,262 S | 3/2011 | Rossi |
| 7,935,142 B2 | 5/2011 | Gregorich |
| 7,942,922 B2 | 5/2011 | Addonizio et al. |

(56) References Cited

U.S. PATENT DOCUMENTS

| | | |
|---|---|---|
| 7,947,071 B2 | 5/2011 | Schmid et al. |
| 7,951,187 B2 | 5/2011 | Ley et al. |
| 7,951,188 B2 | 5/2011 | Ainsworth et al. |
| 7,967,852 B2 | 6/2011 | Addonizio et al. |
| 7,980,289 B2 | 7/2011 | Banas et al. |
| 7,988,718 B2 | 8/2011 | Ehr et al. |
| 7,993,388 B2 | 8/2011 | Lee et al. |
| 8,002,815 B2 | 8/2011 | Laroya et al. |
| 8,007,527 B2 | 8/2011 | Thompson |
| 8,012,195 B2 | 9/2011 | Jang |
| 8,025,694 B2 | 9/2011 | Strauss et al. |
| 8,034,097 B2 | 10/2011 | Neuss et al. |
| 8,043,358 B2 | 10/2011 | Weber et al. |
| 8,043,364 B2 | 10/2011 | Lombardi et al. |
| 8,048,142 B2 | 11/2011 | Venturelli |
| 8,052,738 B2 | 11/2011 | Craven |
| 8,057,531 B2 | 11/2011 | Huang et al. |
| 8,070,792 B2 | 12/2011 | Gregorich et al. |
| 8,105,373 B2 | 1/2012 | Girton et al. |
| 8,114,149 B2 | 2/2012 | Fischell et al. |
| 8,142,489 B2 | 3/2012 | Doran et al. |
| 8,211,162 B2 | 7/2012 | Tischler et al. |
| 8,236,047 B2 | 8/2012 | Thompson |
| 9,066,825 B2 | 6/2015 | Chanduszko |
| 2001/0016770 A1 | 8/2001 | Allen et al. |
| 2001/0027339 A1 | 10/2001 | Boatman et al. |
| 2002/0016623 A1 | 2/2002 | Kula et al. |
| 2002/0045933 A1 | 4/2002 | Jang |
| 2002/0052647 A1 | 5/2002 | Rolando et al. |
| 2002/0095206 A1 | 7/2002 | Addonizio et al. |
| 2002/0107562 A1 | 8/2002 | Hart et al. |
| 2003/0014102 A1* | 1/2003 | Hong .................. A61F 2/91 623/1.15 |
| 2003/0040790 A1 | 2/2003 | Furst |
| 2003/0055485 A1 | 3/2003 | Lee et al. |
| 2003/0120336 A1 | 6/2003 | Thompson |
| 2003/0158596 A1 | 8/2003 | Ikeuchi et al. |
| 2003/0229391 A1 | 12/2003 | Thompson |
| 2004/0088039 A1 | 5/2004 | Lee et al. |
| 2004/0088043 A1 | 5/2004 | Klein |
| 2004/0093058 A1 | 5/2004 | Cottone et al. |
| 2004/0230292 A1 | 11/2004 | Moore |
| 2004/0254627 A1 | 12/2004 | Thompson et al. |
| 2005/0004656 A1 | 1/2005 | Das |
| 2005/0131519 A1 | 6/2005 | Hartley |
| 2007/0073384 A1 | 3/2007 | Brown et al. |
| 2007/0088429 A1 | 4/2007 | Thompson |
| 2007/0213810 A1 | 9/2007 | Newhauser et al. |
| 2007/0239263 A1 | 10/2007 | Fliedner |
| 2008/0051876 A1 | 2/2008 | Ta et al. |
| 2008/0086194 A1 | 4/2008 | Kreidler et al. |
| 2008/0269873 A1 | 10/2008 | Israel et al. |
| 2008/0319528 A1 | 12/2008 | Yribarren et al. |
| 2009/0043374 A1 | 2/2009 | Nakano |
| 2009/0099642 A1 | 4/2009 | Lerdahl et al. |
| 2009/0105809 A1* | 4/2009 | Lee .................. A61F 2/91 623/1.17 |
| 2009/0187239 A1 | 7/2009 | Goto |
| 2010/0094405 A1 | 4/2010 | Cottone |
| 2010/0137974 A1 | 6/2010 | Chouinard et al. |
| 2010/0173066 A1 | 7/2010 | Mangiardi et al. |
| 2010/0217380 A1 | 8/2010 | Donovan et al. |
| 2010/0228338 A1 | 9/2010 | Thompson |
| 2010/0249904 A1 | 9/2010 | Takayuki et al. |
| 2011/0106239 A1 | 5/2011 | Goto |
| 2011/0213457 A1 | 9/2011 | Rolando et al. |
| 2011/0257727 A1 | 10/2011 | Kim et al. |
| 2011/0288633 A1 | 11/2011 | Thompson |
| 2012/0016458 A1* | 1/2012 | Abunassar .......... A61F 2/89 623/1.15 |
| 2012/0172971 A1 | 7/2012 | Lee et al. |
| 2012/0172974 A1 | 7/2012 | Feng et al. |
| 2012/0226346 A1 | 9/2012 | Boismier et al. |
| 2012/0271406 A1 | 10/2012 | Thompson |
| 2013/0304192 A1 | 11/2013 | Chanduszko |

FOREIGN PATENT DOCUMENTS

| | | |
|---|---|---|
| EP | 0421729 A2 | 4/1991 |
| EP | 0540290 A2 | 5/1993 |
| EP | 0606165 A1 | 7/1994 |
| EP | 0887051 A1 | 12/1998 |
| WO | 1996003092 A1 | 2/1996 |
| WO | 1997013475 A1 | 4/1997 |
| WO | 1998022159 A2 | 5/1998 |
| WO | 1998030172 A1 | 7/1998 |
| WO | 1998058600 A1 | 12/1998 |
| WO | 1999015108 A2 | 4/1999 |
| WO | 1999016387 A1 | 4/1999 |
| WO | 1999036002 A1 | 7/1999 |
| WO | 1999049810 A1 | 10/1999 |
| WO | 1999062430 A1 | 12/1999 |
| WO | 2000002502 A1 | 1/2000 |
| WO | 2000006051 A1 | 2/2000 |
| WO | 2001021105 A1 | 3/2001 |
| WO | 2002056795 A2 | 7/2002 |
| WO | 2003024363 A1 | 3/2003 |
| WO | 2003082151 A2 | 10/2003 |
| WO | 2006116383 A2 | 11/2006 |
| WO | 2007059483 A2 | 5/2007 |
| WO | 2007147156 A1 | 12/2007 |
| WO | 2008124728 A1 | 10/2008 |
| WO | 2010030766 A1 | 3/2010 |
| WO | 2010118432 A1 | 10/2010 |
| WO | 2011040218 A1 | 4/2011 |

OTHER PUBLICATIONS

U.S. Appl. No. 13/797,747, filed Mar. 12, 2013 Non-Final Office Action dated Jul. 3, 2014.

U.S. Appl. No. 29/448,505, filed Mar. 12, 2013 Non-Final Office Action dated Oct. 3, 2013.

\* cited by examiner

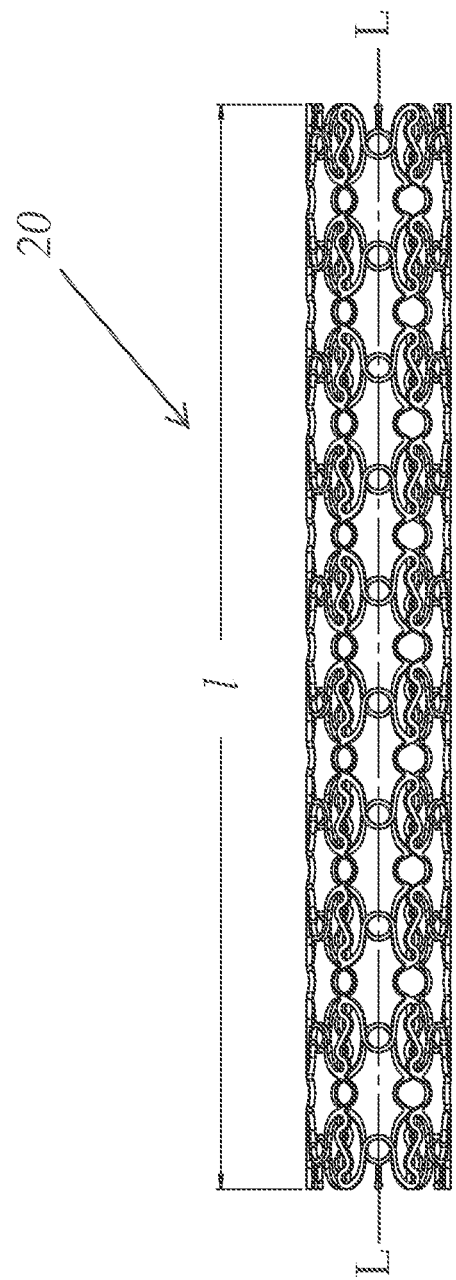

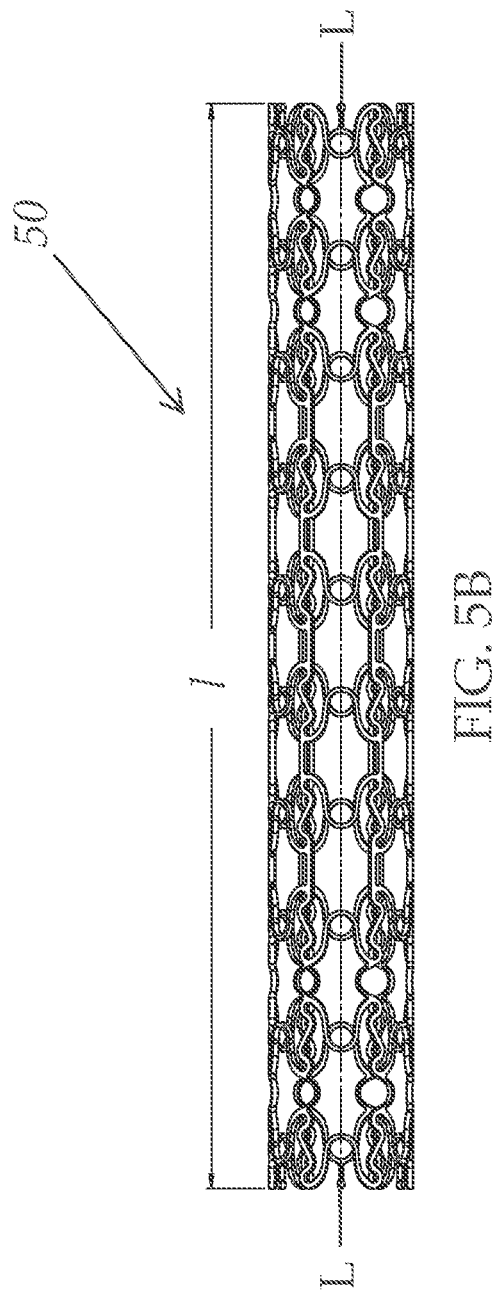

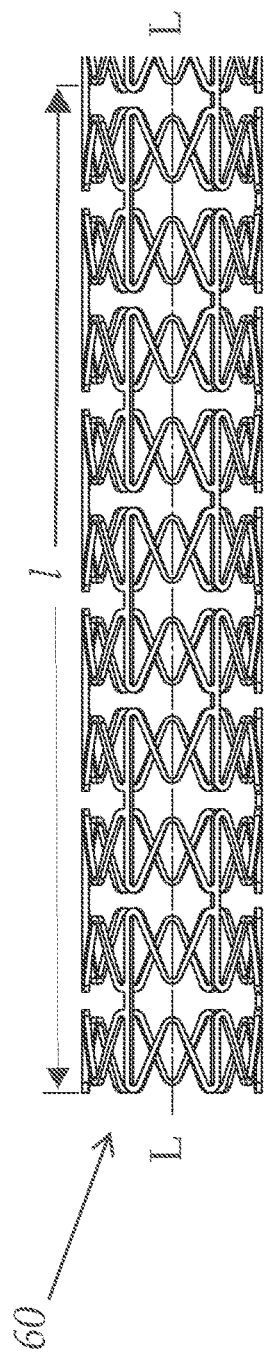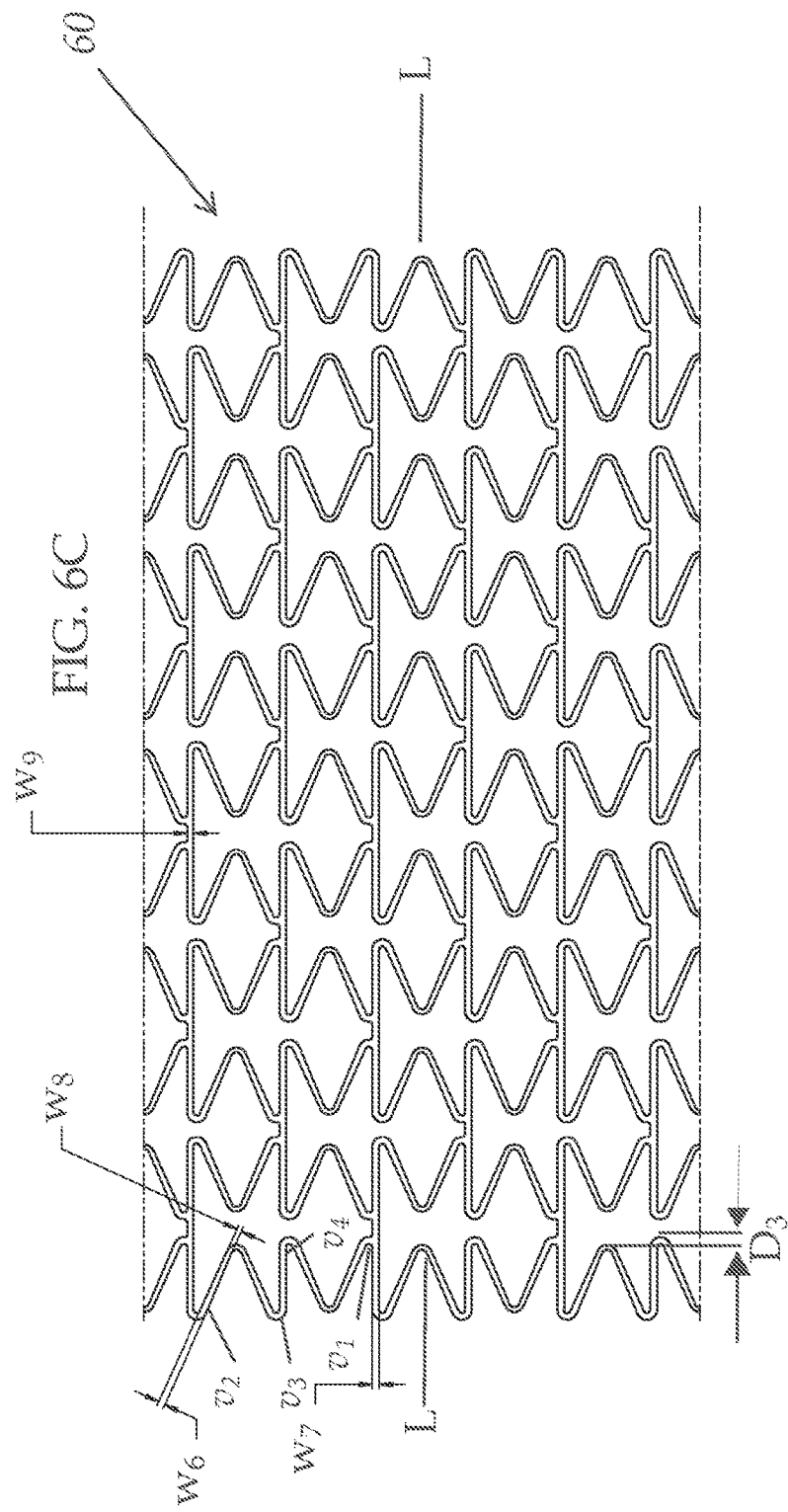
FIG. 6B
FIG. 6C

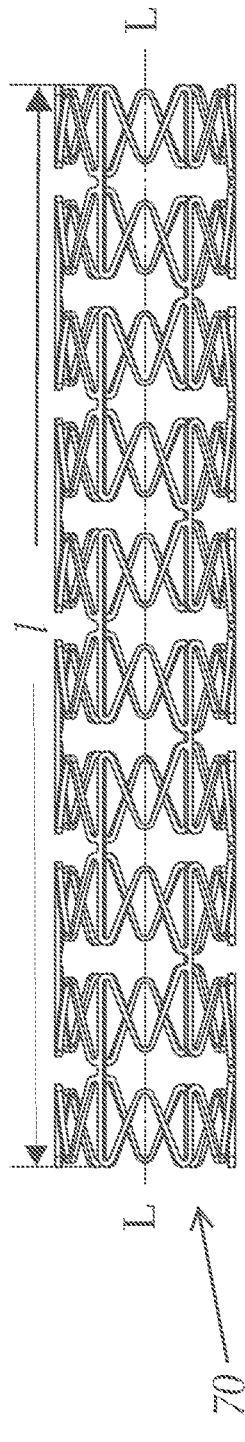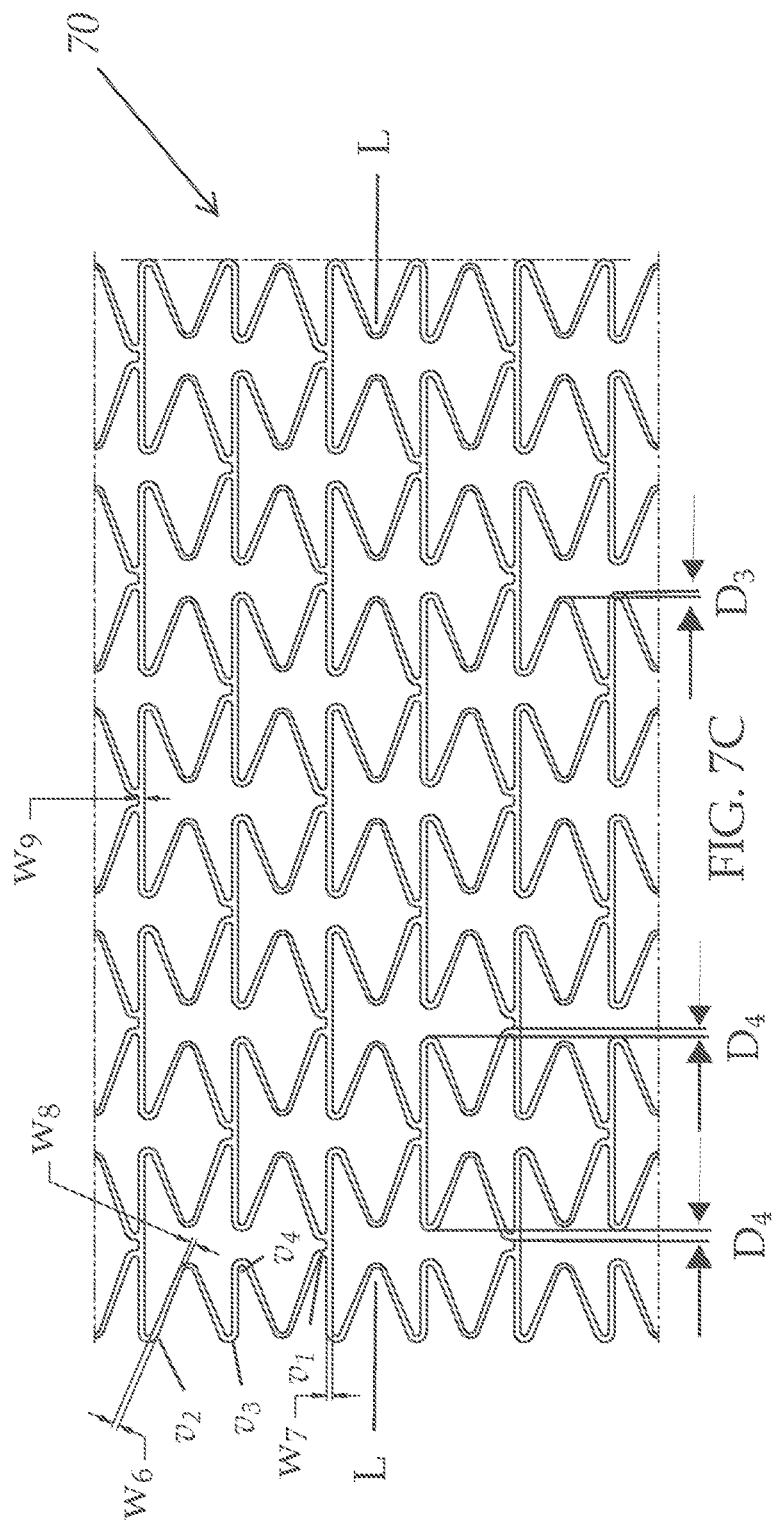
FIG. 7B
FIG. 7C

US 10,588,765 B2

UNIFORMLY EXPANDABLE STENT

PRIORITY

This application is a divisional of U.S. application Ser. No. 13/797,747, filed Mar. 12, 2013, now U.S. Pat. No. 9,066,825, which claim the benefit of priority to the following three applications: 1) U.S. Provisional Application No. 61/646,806, filed May 14, 2012; 2) U.S. Provisional Application No. 61/678,485, filed Aug. 1, 2012; and 3) U.S. Provisional Application No. 61/708,445, filed Oct. 1, 2012, each of which is incorporated by reference in its entirety into this application.

BACKGROUND

Intraluminal prostheses used to maintain, open, or dilate blood vessels are commonly known as stents. Stents have been developed for use in various lumens of the body, including, for example, the biliary tree, venous system, peripheral arteries, and coronary arteries. Stent constructions generally include cylindrical frames that define a plurality of openings.

There are two broad classes of stents: self-expanding stents and balloon expandable stents. Self-expanding stents are typically characterized by intraluminal expansion when a constraining force is removed, such as an outer sheath of a stent delivery system, anchor in the presence of an elevated temperature (due to material properties thereof). Self-expanding stents are generally loaded into a stent delivery system by collapsing the stent from an expanded configuration at a first larger diameter to a collapsed configuration at a second smaller diameter. Balloon expandable stents are typically characterized by intraluminal expansion via an inflation force, such as a balloon catheter. Balloon expandable stents are generally loaded onto a balloon catheter through a crimping process to transition the stent to a collapsed configuration, and are plastically deformed when the balloon is inflated in the body vessel to the expanded configuration.

There are two basic architectures for stents, circumferential and helical. Circumferential configurations generally include a series of cylindrical rings, formed by a series of connected struts, joined together by connecting elements or bridges along a longitudinal axis of the stent. Helical configurations include a continuous helical structure along the longitudinal axis of the stent with adjacent windings, formed by a series of connected struts, connected by one or more connecting elements or bridges.

Stents for use in the arterial and venous systems can be made by machining a pattern of struts and connecting elements from a metal tube, typically by laser machining the pattern into the tube. The pattern of struts and connecting elements can be configured depending on the desired attributes. For example, the pattern can be configured to enhance flexibility or bendability. The pattern can also be configured to ensure uniform expansion and prevent foreshortening of the stent upon intraluminal expansion.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube. Grafts can also be created from fibers woven or knitted into a generally tubular shape. Stents may be fully or partially covered with a graft material, such as ePTFE, on the stent's luminal surface, abluminal surface or both luminal and abluminal surfaces.

Stents may include image enhancing features so that they can be viewed fluoroscopically following intraluminal deployment. Examples of such features include radiopaque markers attached to the stent or integral with the stent, or attached to the one or more graft layers associated with the stent. The image enhancing features generally include a material that is highly visible under fluoroscopy, such as gold, platinum, tantalum, and alloys thereof.

SUMMARY

Intraluminal prostheses including stent architectures are described herein. In one embodiment, a stent architecture includes a series of stent elements repeating along a circumferential axis, the stent elements including v-shaped stent elements having a first leg portion, a second leg portion, and a peak portion, the v-shaped stent elements having at least four different orientations, and V-shaped stent elements connecting adjacent v-shaped stent elements such that the second leg portion of each of the v-shaped stent elements is connected to a V-shaped element, the second leg portion of each of the v-shaped stent elements narrowing in width toward the V-shaped stent element. In one embodiment, the first leg portion of each of the v-shaped stent elements is parallel to a longitudinal axis of the stent architecture. In one embodiment, the stent architecture includes a plurality of series of stent elements, adjacent series of stent elements connected by a plurality of connectors. In one embodiment, the plurality of connectors are straight and connect peak portions of select v-shaped stent elements of adjacent series of stent elements. In one embodiment, the connectors have a width equal to a width of the first leg portion of the v-shaped stent elements.

In one embodiment, the peak portion of a first orientation of the v-shaped stent element is longitudinally spaced a distance from the peak portion of a second orientation of the v-shaped stent element, wherein the first orientation and second orientation are adjacent to one another. In one embodiment, the v-shaped stent elements has four orientations and the peak portion of each of the four orientations of the v-shaped stent element is longitudinally spaced a distance from the peak portion of its adjacent v-shaped stent element. In one embodiment, the distance is in the range from about 0.005 inch to about 0.035 inch.

In one embodiment, the adjacent series of v-shaped and V-shaped stent elements are connected by a plurality of connectors. In one embodiment, the connectors include a radius of curvature and are generally curved. In one embodiment, the curved connectors have a first orientation and a second orientation opposite of the first orientation. In one embodiment, the first orientation of the curved connectors are aligned along a connector circumferential axis, and the second orientation of curved connectors are aligned along an adjacent connector circumferential axis, the aligned first orientation of the curved connectors and aligned second orientation of the curved connectors alternating along a longitudinal axis of the stent architecture. In one embodiment, the first orientation of the curved connectors and second orientation of the curved connectors alternate along each circumferential axis. In one embodiment, the curved connectors have a width less than any width of the v-shaped stent elements and the V-shaped stent elements.

In one embodiment, the stent architecture includes zig-zag rings attached to proximal end and a distal end thereof.

In one embodiment, a stent architecture includes a plurality of zig-zag rings, each ring including a series of stent elements repeating along a circumferential axis, the stent elements including first, second, third, and fourth stent elements connected by first, second, third, and fourth peak portions, adjacent zig-zag rings connected by a plurality of connectors to form stent cells, the stent cells along a circumferential axis having the same shape, the shape of the stent cells along a first circumferential axis different from the shape of the stent cells along an adjacent second circumferential axis. In one embodiment, the stent elements of a first zig-zag ring are a mirror image of the stent elements of a second adjacent zig-zag ring.

In one embodiment, a stent architecture having a plurality of stent cells, including a series of stent elements repeating along a circumferential axis, the stent elements including R-shaped stent elements having at least four different orientations, the R-shaped stent elements having at least a first straight portion, and U-shaped stent elements having at least two different orientations, the U-shaped stent elements connecting adjacent R-shaped stent elements such that the first straight portion of each of the R-shaped stent elements is connected to a U-shaped stent element, the first straight portion of each of the R-shaped stent elements narrowing in width toward the U-shaped stent element. In one embodiment, the R-shaped stent elements include at least first, second, third and fourth curved radius portions. In one embodiment, the plurality of stent cells includes a first stent cell and a second stent cell different from the first stent cell, the first and second stent cells alternating along the circumferential axis.

In one embodiment, the R-shaped stent elements include a first R-shaped stent element in a first orientation, a second R-shaped stent element in a second orientation different from the first orientation, a third R-shaped stent element oriented in a third orientation different from the first and second orientations, and a fourth R-shaped stent element in a fourth orientation different from the first, second, and third orientations. In one embodiment, the U-shaped gent elements include a first U-shaped stent element in a first orientation and a second U-shaped stent element oriented in a second orientation different from the first orientation. In one embodiment, the first R-shaped stent element is connected to the second U-shaped stent element and the second R-shaped stent element, wherein the second R-shaped stent element is connected to the first R-shaped stent element and the first U-shaped stent element, wherein the first U-shaped stent element is connected to the second R-shaped stent element and the third R-shaped stent element, wherein the third R-shaped stent element is connected to the first U-shaped stent element and the fourth R-shaped stent element, and wherein the fourth R-shaped stent element is connected to the third R-shaped stent element and the second U-shaped stent element.

In one embodiment, the stent architecture includes a plurality of connectors connecting adjacent series of stent elements. In one embodiment, the adjacent series of stent elements and the connectors define stent cells. In one embodiment, a first stent cell pattern and a second stent cell pattern alternate along a circumferential axis. In one embodiment, the first and second stent cell patterns are longitudinally offset along a longitudinal axis of the stent architecture.

In one embodiment, the connectors connect the first R-shaped stent element in a first series of stent elements to the third R-shaped stent element in a second adjacent series of stent elements. In one embodiment, the connectors further connect the fourth R-shaped stent element in the first series of stent elements to the second R-shaped stent element in the second adjacent series of stent elements. In one embodiment, the plurality of connectors are attached to one of a first, second, third, and fourth curved radius portions of the R-shaped stent elements. In one embodiment, the connectors connect the first U-shaped stent element in the first series of stent elements to the second U-shaped stent element in the second adjacent series of stent elements.

In one embodiment, the connectors connecting the R-shaped stent elements include a radius of curvature and are generally curved. In one embodiment, the curved connectors have a first orientation and a second orientation opposite of the first orientation. In one embodiment, the first orientation of the curved connector is convex and the second orientation of the curved connector is concave for a given perspective. In one embodiment, the first orientation of the curved connectors are aligned along a connector circumferential axis, and the second orientation of curved connectors are aligned along an adjacent connector circumferential axis, the aligned first orientation of the curved connectors and aligned second orientation of the curved connectors alternating along a longitudinal axis of the stent architecture. In one embodiment, the first orientation of the curved connectors and second orientation of the curved connectors alternate along each circumferential axis. In one embodiment, the connectors connecting the R-shaped stent elements are straight. In one embodiment the connectors at the ends of the stent architecture are curved and the connectors in the middle of the stent architecture are straight.

In one embodiment, the straight connectors connect the first U-shaped stent element in the first series of stent elements to the second U-shaped stent element in the second adjacent series of stent elements.

In one embodiment, the stent architecture includes receiving members extending from one or both ends. In one embodiment, the receiving members are shaped to receive a radiopaque element. In one embodiment, the receiving members include a post portion and an enlarged portion. In one embodiment, the receiving members include a bore or opening sized to receive a radiopaque element therein.

In one embodiment, a stent architecture includes a plurality of stent cells, the stent cells including a series of stent elements repeating along a circumferential axis, the stent elements including R-shaped stent elements having at least a first straight portion, and U-shaped stent elements connecting adjacent R-shaped stent elements such that the first straight portion of each of the R-shaped stent elements is connected to a U-shaped element, the first straight portion of each of the R-shaped stent elements narrowing in width toward the U-shaped stent element. In one embodiment, the plurality of stent cells includes a first stent cell and a second stent cell different from the first stent cell, the first and second stent cells alternating along the circumferential axis.

In one embodiment, an intraluminal prosthesis includes a stent architecture formed by machining a tube, the stent architecture having a plurality of stent cells with a plurality of connectors connecting the stent cells, the stent cells including a series of stent elements repeating along a circumferential axis, the stent elements including R-shaped stent elements having at least first, second, third and fourth curved radius portions, the R-shaped stent elements having at least four different orientations, and U-shaped stent elements having at least two different orientations, the U-shaped stent elements connecting select adjacent R-shaped stent elements. In one embodiment, the R-shaped stent elements include a first R-shaped stent element in a first orientation, a second R-shaped stent element in a second orientation different from the first orientation, a third R-shaped stent element oriented in a third orientation different from the first and second orientations, and a fourth R-shaped stent element in a fourth orientation different from the first, second, and third orientations. In one embodiment, the U-shaped stent elements include a first U-shaped stent element in a first orientation and a second U-shaped stent element oriented in a second orientation different from the first orientation. In one embodiment, the first R-shaped stent element is connected to the second U-shaped stent element and the second R-shaped stent element, wherein the second R-shaped stent element is connected to the first R-shaped stent element and the first U-shaped stent element, wherein the first U-shaped stent element is connected to the second R-shaped stent element and the third R-shaped stent element, wherein the third R-shaped stent element is connected to the first U-shaped stent element and the fourth R-shaped stent element, and wherein the fourth R-shaped stent element is connected to the third R-shaped stent element and the second U-shaped stent element. In one embodiment, each R-shaped stent element includes at least a first straight portion that narrows in width toward the connected U-shaped stent element.

The stent architectures according to embodiments described herein may include a covering. In one embodiment, the covering includes one or more graft layers attached to the stent architecture. In one embodiment, the one or more graft layers include an inner expanded polyfluoroethylene (ePTFE) graft layer and an outer ePTFE graft layer. In one embodiment, the inner ePTFE graft layer and the outer ePTFE graft layer are positioned over the stent architecture as extruded tubes of unsintered ePTFE, and are sintered together through openings in the stent.

BRIEF DESCRIPTION OF THE DRAWINGS

FIG. 2B is a top view of the stent embodiment of FIG. 2A in an as-cut configuration.

FIG. 5B is a top view of the stent embodiment of FIG. 5A in an as-cut configuration.

FIG. 6B is a top view of the stent embodiment of FIG. 6A in an as-cut configuration.

FIG. 6C is a flat view of the stent embodiment of FIG. 6A indicating various dimensions.

FIG. 7B is a top view of the stent embodiment of FIG. 7A in an as-cut ion.

FIG. 7C is a flat view of the stent embodiment of FIG. 7A indicating various dimensions.

DESCRIPTION

Figure 1A:
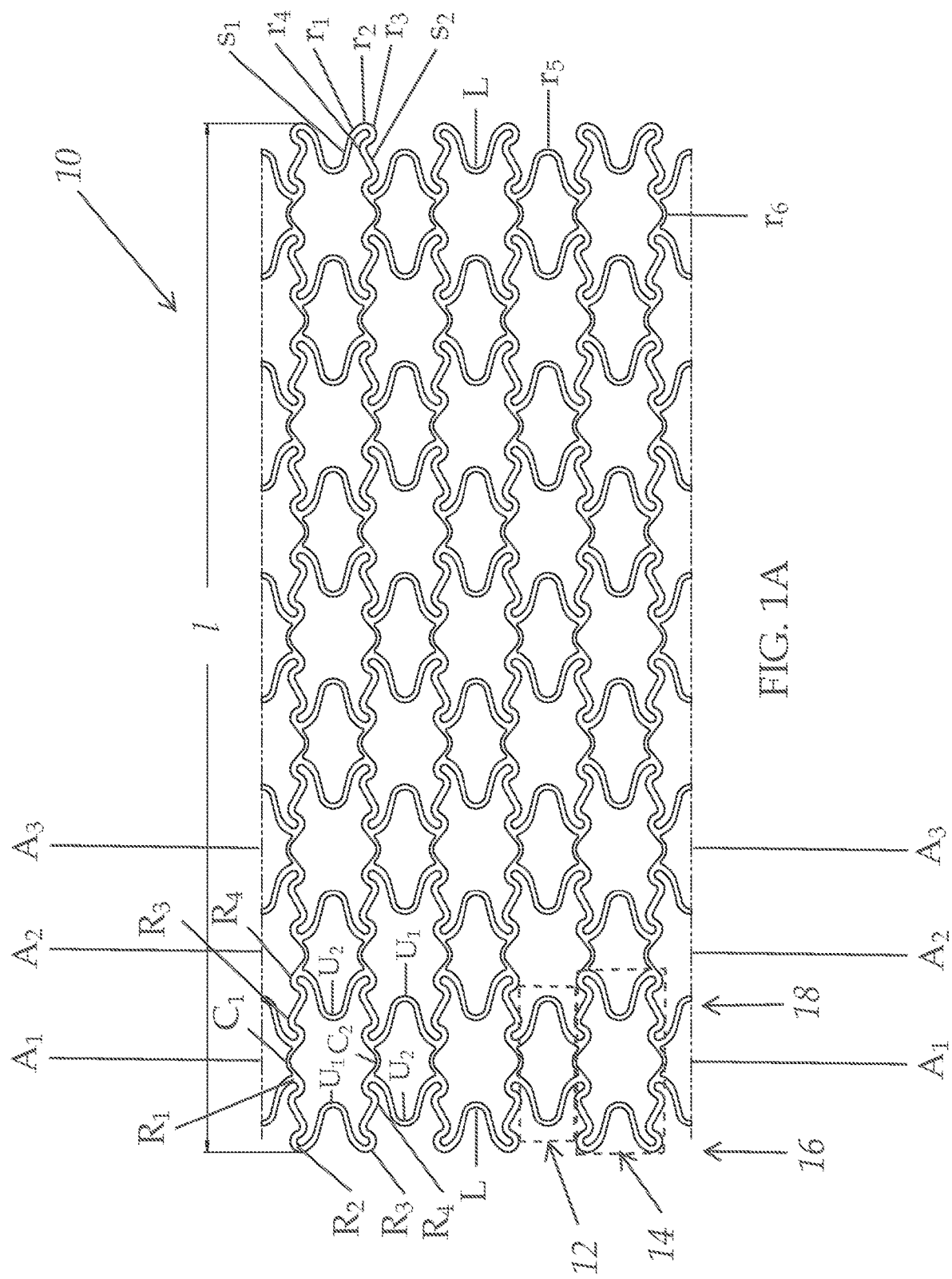
FIG. 1A is a flat view of a stent embodiment in an expanded configuration.

The following description and accompanying figures, which describe and show certain embodiments, are made to demonstrate, in a non-limiting manner, several possible configurations of an expandable stent frame according to various aspects and features of the present disclosure. The patterns shown and described herein may be incorporated into any intraluminal prosthesis, such as a self-expanding stent or a balloon expandable stent, without limitation. In one embodiment, the patterns disclosed herein may be machined (e.g., laser machined) into a seamless tube of metal or polymer. Non-limiting examples of potential metal tubes include stainless steel (e.g. AISI 316 SS), titanium, cobalt-chromium alloys, and nickel titanium (nitinol). In other embodiments, the patterns disclosed herein may be formed into a sheet of metal or polymer that is rolled into a tubular shape. The tubes or sheets may be heat-treated prior to machining the pattern therein, and the machined tubes or sheets may be annealed and/or electro-polished. Other known pre-processing and post-processing methods are also contemplated herein.

As used herein, the term "stent architecture" means the various features of the stent that contribute to its form, including the pattern in the stent wall. The term "stent cell" means a portion of the pattern in the stent wall that may be repeating along a circumferential and/or longitudinal path.

The stents described herein may be covered by one or more graft layers. The presence of a graft layer on the luminal surface and/or abluminal surface of a stent may influence the design of the stent architecture. For example, the expansion behavior of the stent may be tailored to avoid tearing or ripping of the graft material during deployment. It has been observed that the greater the uniformity of stent expansion, the fewer issues with graft tearing, detachment, etc. Another consideration that may influence the design of the stent architecture include excessive foreshortening of the stent during expansion from a collapsed delivery configuration to an expanded deployed configuration, which can lead to inaccurate stent deployment. Still other considerations include flexibility of the stent and patency of the stent in vivo, and minimal profile of the stent in the collapsed delivery configuration.

In certain embodiments described herein, the stent architecture is designed to prevent excessive foreshortening (i.e., the stent gets shorter as it transitions from the collapsed configuration to the expanded configuration), which can lead to inaccurate stent deployment in a body vessel, and to ensure uniform radial expansion. For example, it has been discovered that narrowing of the strut width at strategic locations in a given stent cell promotes uniform expansion of the stent cell.

Intraluminal prostheses described herein ma include stents encapsulated by a graft material, as described in U.S. Pat. Nos. 5,749,880 and 6,124,523, each of which is incorporated by reference in its entirety into this application. In one embodiment, an inner ePTFE graft layer is positioned over a mandrel. In one embodiment, the inner ePTFE graft layer placed over the mandrel is an extruded tube of unsintered ePTFE. The stent is placed over the inner ePTFE graft layer so that the luminal (inner) surface of the stent contacts the inner ePTFE graft layer, and an outer ePTFE graft layer is positioned over the abluminal (outer) surface of the stent. In one embodiment, the outer ePTFE graft layer placed over the stent is also an extruded tube of unsintered ePTFE. In one embodiment the inner and outer ePTFE graft layers are extruded at their encapsulation diameters (i.e., neither are radially manipulated prior to encapsulation). In one embodiment, the encapsulation diameters are about 4 mm. In one embodiment, the stent is fully encapsulated along its length such that both proximal and distal ends of the stent are covered by ePTFE graft material. In one embodiment, the stent is encapsulated at a diameter slightly smaller than the as-cut diameter but larger than the collapsed delivery diameter.

One or more PTFE tape layers may then be wrapped over the outer ePTFE graft layer, and the assembly is placed in a heating device, such as an oven, to sinter the inner and outer ePTFE graft layers together through the openings in the stent architecture. Following the sintering step, the PTFE tape layer(s) are removed and the stent-graft is crimped (in the case of a balloon expandable stent) or collapsed (in the case of a self-expanding stent) into its collapsed configuration. In one embodiment, the inner ePTFE graft layer and outer ePTFE grail layer have the same microstructure and thickness. In one embodiment, the microstructure includes a uniaxial fibril orientation. In one embodiment, the inner and outer ePTFE graft layers have an internodal distance (IND) in the range from about 10 µm to about 40 µm. In one embodiment, each of the inner and outer ePTFE graft layers has a thickness in the range from about 0.07 mm to about 0.13 mm. In one embodiment, each of the inner and outer ePTFE graft layers each has a thickness in the range from about 0.10 mm to 0.15 mm, preferably about 0.14 mm.

In one embodiment, the stent-graft assembly may be reinforced with a middle ePTFE graft layer, including spaced apart rings or strips of ePTFE of about 2 mm wide positioned at the proximal end of the stent-graft, the center of the stent-graft, and the distal end of the stent-graft. The middle ePTFE graft layer may be sintered ePTFE material. Examples of interlayer members are described in U.S. Pat. No. 6,451,047, which is incorporated by reference in its entirety into this application. The middle ePTFE graft layer may have the same node alignment as the inner and outer ePTFE graft layers or may be different therefrom for example perpendicular or at a 45° angle.

The drawings herein indicated as showing the various stents in an expanded configuration are laid flat depictions of the stents following formation of the pattern, for example by laser machining a tube of polymer or metal material. This is one possible expanded configuration shown for ease of reference. It should be appreciated that, depending on the size of the vessel in which the stents described herein is inserted, the stent could be expanded to a diameter larger than the diameter depicted, which would slightly alter the shape and/or relationship of stent elements and/or connectors to one another (e.g., aspects of the stent that are parallel to the longitudinal axis of the stent may be oblique at larger expanded diameters). The drawings indicated as showing the various stents in an as-cut configuration are top views of the stent following formation thereof, for example, by laser machining a metal or polymer tube. In one embodiment, the stent architectures and patterns described herein are formed in a tube having a diameter of about 4.8 mm. In one embodiment, the stent architectures and patterns described herein are formed in a tube having a diameter of about 6.4 mm. Of course, these are non-limiting examples of tube diameters, as a wide range of tube diameters are contemplated herein. In general, the tube diameter will be selected based on the target vessel diameter for which the stent is intended to be placed (e.g., larger tube diameters will be selected for larger target vessels). The stent embodiments described herein may have a longitudinal length from a proximal end to a distal end, indicated as l in the figures, in the range from about 15 mm to about 70 mm, although shorter and longer lengths are also contemplated without limitation, depending on the particular stent application.

Figure 1B:
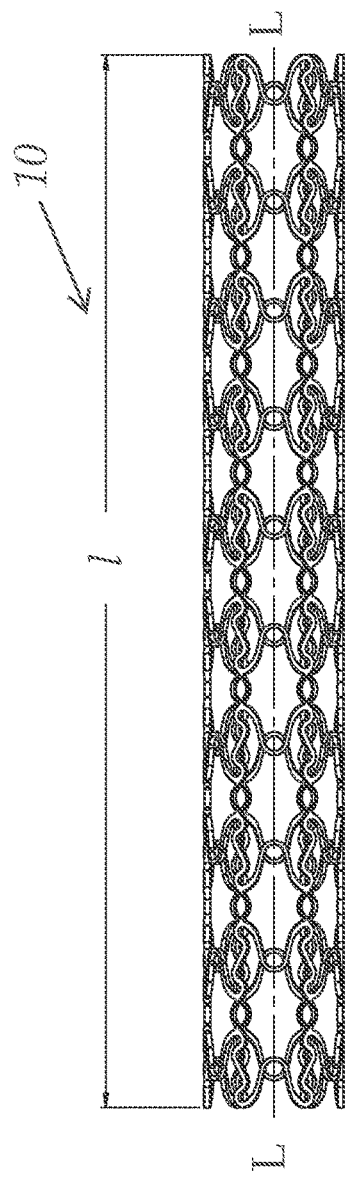
FIG. 1B is a top view of the stent embodiment of FIG. 1A in an as-cut configuration.
Figure 1C:
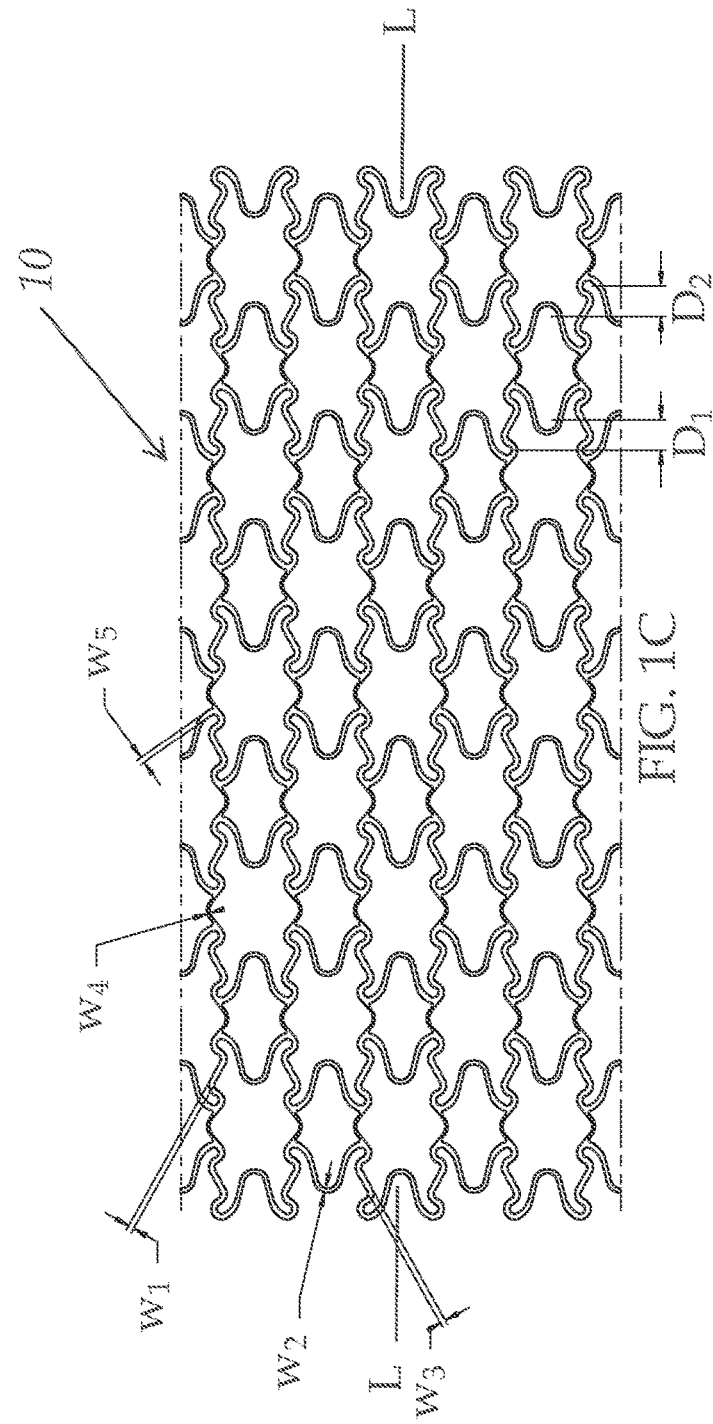
FIG. 1C is a flat view of the stent embodiment of FIG. 1A indicating various dimensions.

Referring to FIGS. 1A-C, a first stent architecture 10 is shown, including a sequentially repeating pattern of stent cells 12 and 14 aligned along a series of circumferential axes perpendicular to a longitudinal axis L. Any number of circumferential axes along which the pattern of stent cells is arranged is possible, depending on various stent dimensional features including, for example, overall stent length, stent cell length, connector length, etc. The stent cells 12 and 14 are formed by stent elements described herein according to the letter resemblance thereof, the stent elements repeating along the circumferential axes. According to one embodiment, the R-shaped stent elements are similar or identical to those described in U.S. Pat. No. 6,821,292, which is incorporated by reference in its entirety into this application.

Beginning from the top left side of FIG. 1A, a repeating series of stent elements is shown along a first side 16 of the stent cells 12 and 14, the stent elements including R shapes and U shapes, i.e., R-shaped stent elements and U-shaped stent elements. Generally, the R-shaped stent elements include a first straight portion $s_1$ followed by a first curved radius portion $r_1$, followed by a second curved radius portion $r_2$, followed by a third curved radius portion $r_3$, followed by a fourth curved radius portion $r_4$, followed by a second straight portion $s_2$. Generally, the U-shaped stent elements include a curved radius portion $r_5$. Stent element $R_1$ is connected to stent element $R_2$, which is connected to stent element $U_1$, which is connected to stent element $R_3$, which is connected to stent element $R_4$, which is connected to stent element $U_2$, which is connected to stent element $R_1$. The stent elements $R_1$, $R_2$, $R_3$, $R_4$ are similar in shape but are oriented differently from one another with respect to a circumferential axis and/or a longitudinal axis. The stent elements $U_1$ and $U_2$ are facing in opposite directions with respect to a circumferential axis. The same repeating series of stent elements (arranged identically with respect to the circumferential axis $A_1$ and longitudinal axis L) proceeds along a second side 18 of the stent cells 12 and 14, but is offset such that the sequence begins with stent element $R_3$ which is directly adjacent $R_1$ of the series along the first side 16. Thus, beginning from the top of FIG. 1A along second side 18, the series of stent elements is $R_3$, $R_4$, $U_2$, $R_1$, $R_2$, $U_1$, $R_3$, etc.

The first side 16 is connected to the second side 18 via connectors $C_1$ and $C_2$ that each include a curved radius portion $r_6$. Stent element $R_1$ of the first side 16 is connected to stent element $R_3$ of the second side by connector $C_1$. In the embodiment shown in FIGS. 1A-C, connector $C_1$ is attached to stent elements $R_1$ and $R_3$ at about the second radius portion $r_2$ and is oriented to be convex with respect to stent cell 12 and concave with respect to stent cell 14. Stent element $R_4$ of the first side 15 is connected to stent element $R_2$ of the second side 18 by connector $C_2$ also at about the second radius portion $r_2$ of each stent element $R_4$ and $R_2$, connector $C_2$ oriented oppositely with respect to connector $C_1$ such that connector $C_2$ is also convex with respect to stent cell 12 and concave with respect to stent cell 14. In other embodiments, the connectors along a given circumferential axis may be only $C_1$ connectors or $C_2$ connectors (e.g., see FIG. 2) such that all connectors are oriented in the same direction.

Beginning from the left side of FIG. 1A and moving toward the right side of FIG. 1A along the longitudinal axis L, stent cells 12 and 14 along circumferential axis $A_1$ are connected to stent cells 12 and 14 along circumferential axis $A_3$ by connectors $C_1$ and $C_2$. More specifically, adjacent stent cells 14 are connected by $C_2$ at stent elements $R_4$ and $R_2$ and by $C_1$ at stent elements $R_1$ and $R_3$ to thereby form a stent cell 12 therebetween. Accordingly, the same stent cell pattern of circumferential axes $A_1$ and $A_3$ is formed along axis $A_2$ offset by one stent cell with respect therewith. It is also noted that the same offset repeating pattern is observed along adjacent longitudinal axes. In the embodiment shown in FIGS. 1A-C, the length of stent cells 12 and 14 (i.e., measured from one point on the longitudinal axis L to a different point on the longitudinal axis L) along circumferential axes $A_1$, $A_2$, $A_3$, etc. are the same along the length 1 of the stent 10. However, it is contemplated for other embodiments that the length of stent cells 12 and/or 14 along a given circumferential axis are longer or shorter than those of an adjacent circumferential axis. For example, in one embodiment, the length of the stent cells 12 and 14 are longer at the ends of the stent and shorter in the middle regions of the stent. Such a configuration provides a stiffer middle and softer ends to facilitate a certain desired expansion pattern. In the same way, although the height of stent cells 12 and 14 (i.e., measured from one point on a circumferential axis to a different point on the circumferential axis) along circumferential axes $A_1$, $A_2$, $A_3$, etc. are the same, it is contemplated that the height of stent cells 12 and 14 could vary along a given circumferential axis or could vary with respect to adjacent circumferential axes.

FIG. 1B is a top view of stent 10. In one embodiment, stent 10 is produced from a metal or polymer tube that is laser machined to form the stent architecture. In one embodiment, the tube has a thickness of about 0.0075 inch and a diameter of about 5 mm. In an embodiment in which stent 10 is covered by one or more graft layers, stent 10 can be expanded to a larger diameter for covering with the graft layer(s), can be covered with the graft layer(s) at the as-cut diameter, or can be crimped to a smaller diameter for covering with the graft layer(s), following post processing steps such as, for example, electro-polishing. The foregoing embodiments are equally applicable to each of the stent architectures described herein.

In the embodiment of FIGS. 1A-C, the width of selected stent elements is narrowed to promote uniform expansion of the stent. As discussed above, such uniform expansion is preferable, for example, for stents covered by graft material to avoid tearing or deformation of the graft material upon deployment. In other embodiments, the thickness of selected stent elements is reduced instead of, or in conjunction with, the narrowing of the width thereof. In the embodiment shown in FIGS. 1A-C, the width of the first straight portion $s_1$ of each stent element $R_1$-$R_4$ of stent 10 tapers or narrows toward the respective stent elements $U_1$ and $U_2$. In other embodiments, the first straight portions $s_1$ of only selected stent elements $R_1$-$R_4$ taper or narrow. In still other embodiments, different portions of the R-shaped elements may have a wider or narrower width than other portions thereof.

In FIG. 1C, widths $w_1$-$w_5$ are shown at different locations on the strut cells. Width $w_1$ is at a section of stent element $R_3$, width $w_2$ is at a section of stent element $U_2$ (which in the embodiment shown is the same width at the corresponding section of stent element $U_1$), width $w_3$ is at a section of stent element $R_2$, width $w_4$ is at a section of connector $C_1$, and $w_5$ is at a section of stent element $R_1$. In the embodiment shown, the widths at $w_1$, $w_3$, and $w_5$ are the same, the width at $w_2$ is less than the widths of $w_1$, $w_3$, and $w_5$, and the width at $w_4$ is less than the width at $w_2$. The width of the straight portion $s_1$ of stent elements $R_1$-$R_4$ narrows or tapers from the first curved radius portion $r_1$ thereof (e.g., width $w_5$) to the stent elements $U_1$-$U_2$ (e.g., width $w_2$) connecting the stent elements $R_1$-$R_4$. In one embodiment, which could be used in a vessel diameter of about 5 mm to about 10 mm (e.g., an iliac artery), the widths of $w_1$, $w_3$ and $w_5$ are in the range from about 0.0050 inch to about 0.0100 inch, for example about 0.0075 inch; the width at $w_2$ is in the range from about 0.0040 inch to about 0.0070 inch, for example about 0.0055 inch; and the width at w4 is in the range from about 0.0025 inch to about 0.0055 inch, for example about 0.0035 inch. For smaller or larger vessels, dimensions can be accordingly smaller or larger.

Also shown in FIG. 1C is the distance $D_1$ and $D_2$ of stent cell 14, where $D_1$ is measured from the center of radius of the curved radius portion $r_3$ of stent element $R_3$ to the center of radius of the curved radius portion $r_5$ of stent element $U_2$, and where $D_2$ is measured from the center of radius of the curved radius portion $r_5$ of stent element $U_1$ to the center of radius of the curved radius portion $r_1$ of stent element $R_4$. In the embodiment shown $D_1$ is equal to $D_2$, but in other embodiments $D_1$ could be greater than or less than $D_2$. In one embodiment the distances $D_1$ and $D_2$ are in the range from about 0.030 inch to about 0.060 inch, for example about 0.040 inch. Stent architectures with similar repeating stent elements and/or connectors, as described herein (e.g., stents 20, 30, 40, 50), could have the same or similar dimensions as those described in connection with stent 10.

Depending on the level of flexibility and bendability desired, the curved connectors $C_1$ and $C_2$ could be thinner (e.g., more flexible) or thicker (e.g., less flexible). Depending on the expansion characteristics desired, the crosssection of the stent elements could be altered. For example, if the R-shaped stent elements and U-shaped stent elements have the same dimensions, the U-shaped stent elements will naturally be more rigid; thus, to promote uniform expansion the U-shaped stent elements could be taller or thinner than the R-shaped stent elements. However, a taller U-shaped stent element could lead to a larger compressed profile, and therefore in the embodiment shown, the U-shaped stent elements have a width thinner than the R-shaped stent elements.

Figure 2A:
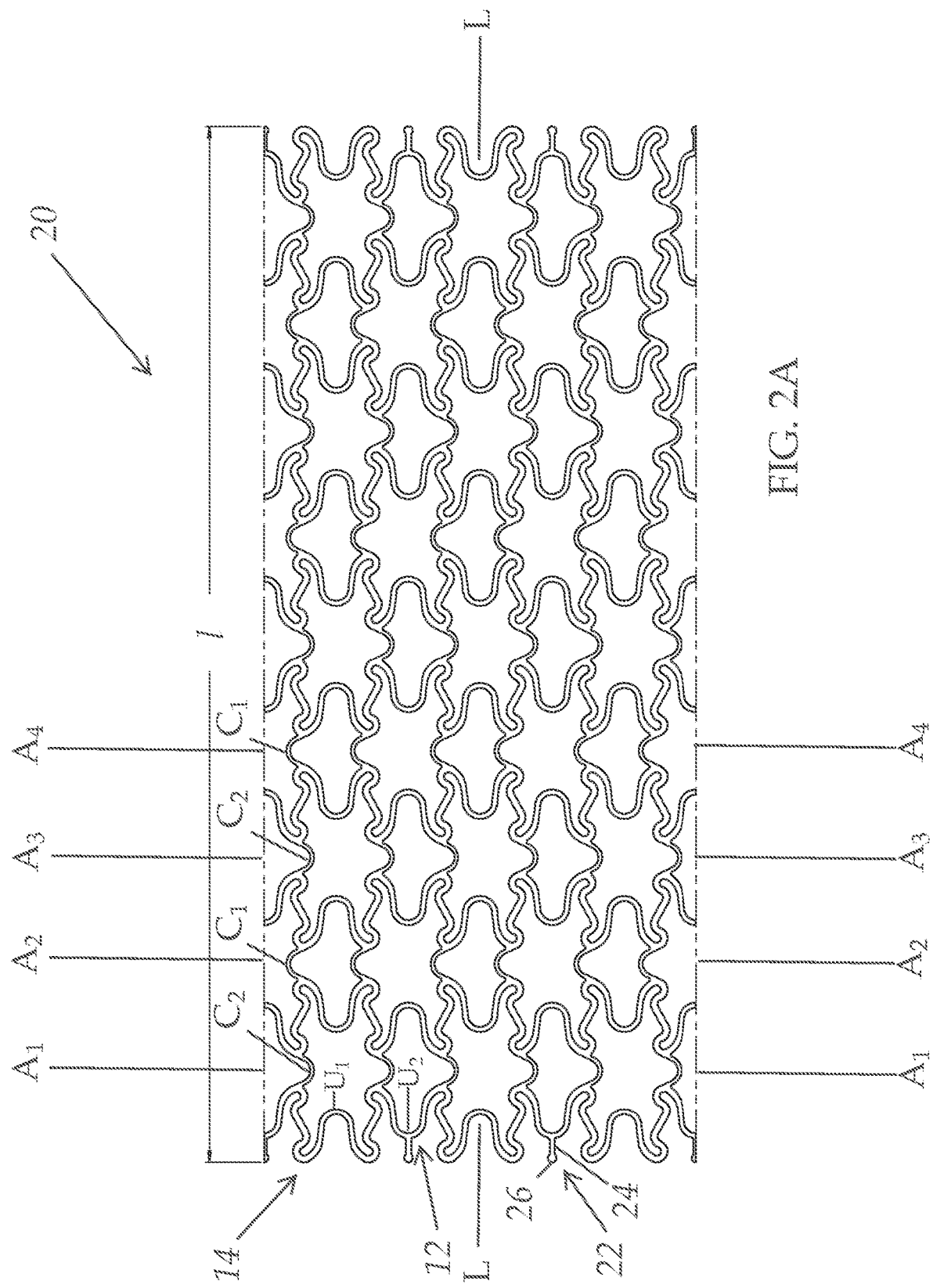
FIG. 2A is a flat view of a stent embodiment in an expanded configuration.

FIGS. 2A-B illustrate stent 20 that has the same repeating stent elements $R_1$-$R_4$ and $U_1$-$U_2$ as stent 10; however, stent 20 differs from stent 10 in at least the following ways. First, the connectors are similarly oriented along each circumferential axis, where along odd-numbered circumferential axes $A_1$, $A_3$, etc. the connectors are $C_2$ connectors, and where along even-numbered circumferential axes $A_2$, $A_4$, etc. the connectors are $C_1$ connectors. In other embodiments, the connectors can be the same along one or more adjacent circumferential axes. In one embodiment, the widths of the stent elements $R_1$-$R_4$ and $U_1$-$U_2$, and the connectors $C_1$ and $C_2$ for stent 20 can be the same as described above in connection with stent 10.

Figure 11A:
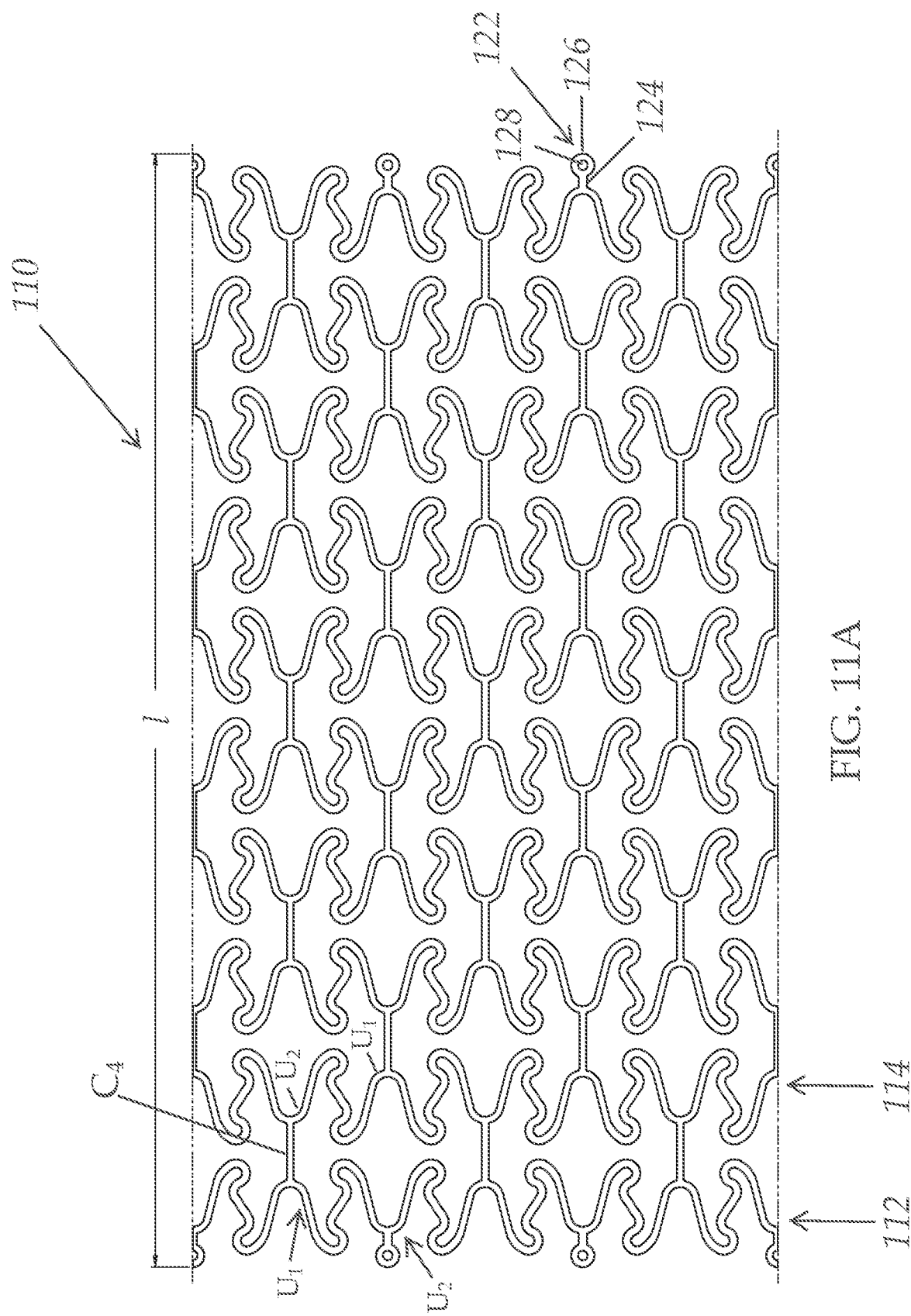
FIG. 11A is a flat view of a stent embodiment in an expanded configuration.
Figure 11B:
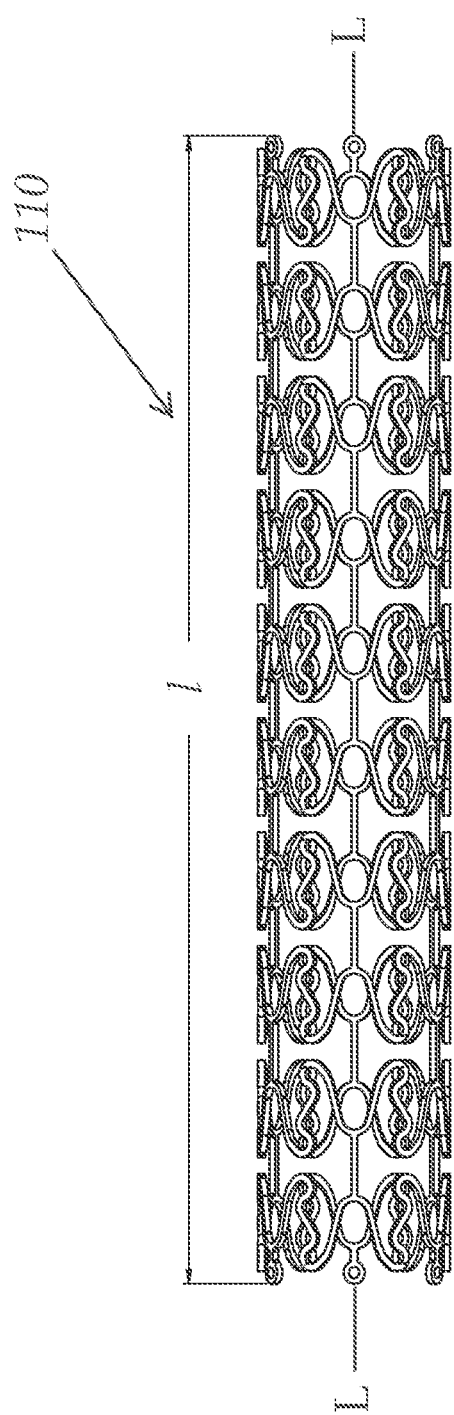
FIG. 11B is a top view of the stent embodiment of FIG. 10A in an as-cut configuration.

Second, stent 20 includes receiving members 22 extending from each of the opposing ends of the stent 20, the members 22 extending from each end stent element $U_2$ of stent cells 12. The receiving members 22 include a post portion 24 and an enlarged portion 26 at the end of the member 22 remote from the stent element $U_2$. In one embodiment, the enlarged portion 26 is sized to receive a radiopaque element, for example, a radiopaque element having a C-shape that fastens to the enlarged portion 26. In other embodiments, the enlarged portion may include a bore or opening sized to receive a radiopaque element therein, as shown in FIGS. 11A-B. In one embodiment, the width of the post portion 24 of the receiving members 22 is about 0.0055 inch, and the width of the enlarged member is about 0.0100. In one embodiment, the post portion 24 has a cylindrical shape and the enlarged portion 26 has a spherical shape or other atraumatic shape to prevent injury to the insertion vessel. As shown in FIGS. 2A-B, the receiving members 22 have a length such that the end thereof aligns circumferentially with the outermost end of the stent elements at each opposing end of stent 20. By aligning the outermost ends of the stent elements and receiving members, in an embodiment including one or more graft layers, the graft layer(s) can be in the form of a tube without altering the ends thereof, the receiving members supporting the tubular ends of the graft layer(s) upon collapse and/or expansion of the stent. It is noted that the receiving members of FIGS. 2A-B could be incorporated into any of the other stent architectures described herein.

FIG. 2B is a top view of stent 20. In one embodiment, stent 20 is produced from a metal or polymer tube that is laser machined to form the stent architecture.

Figure 3A:
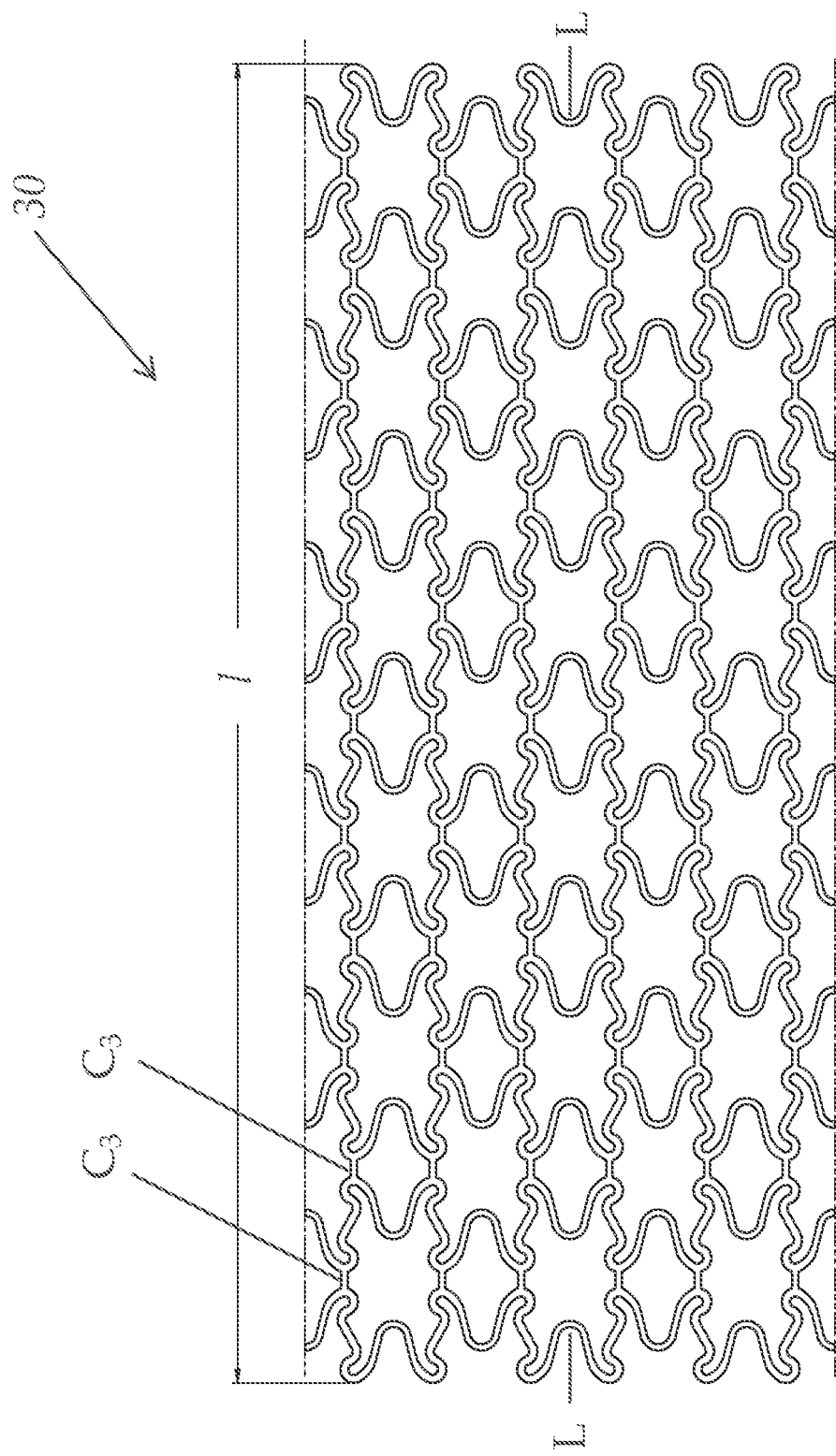
FIG. 3A is a flat view of a stent embodiment in an expanded configuration.
Figure 3B:
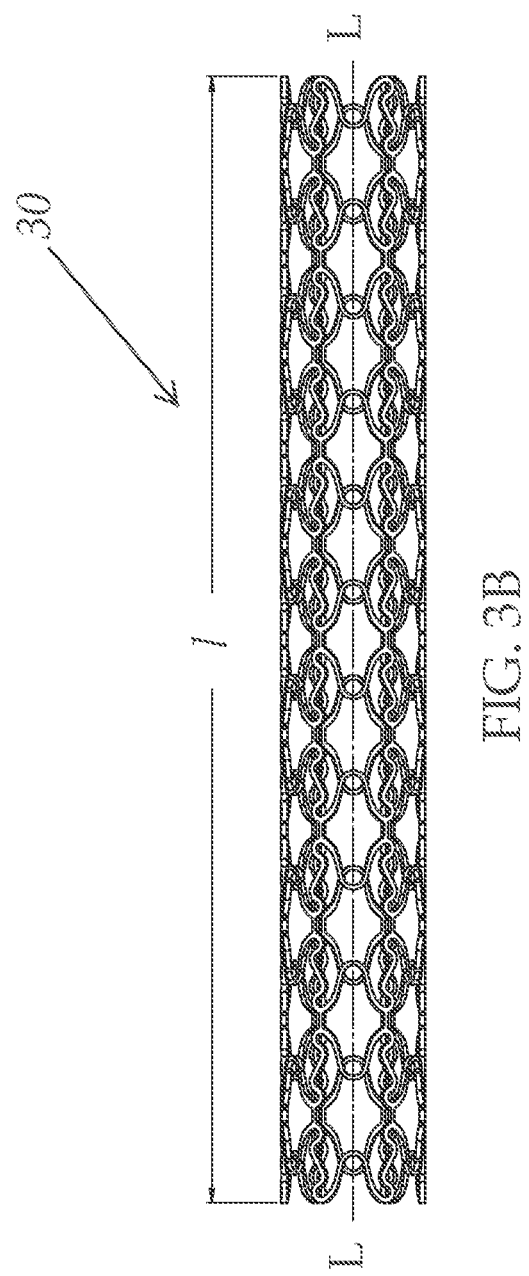
FIG. 3B is a top view of the stent embodiment of FIG. 1A in an as-cut configuration.
Figure 3C:
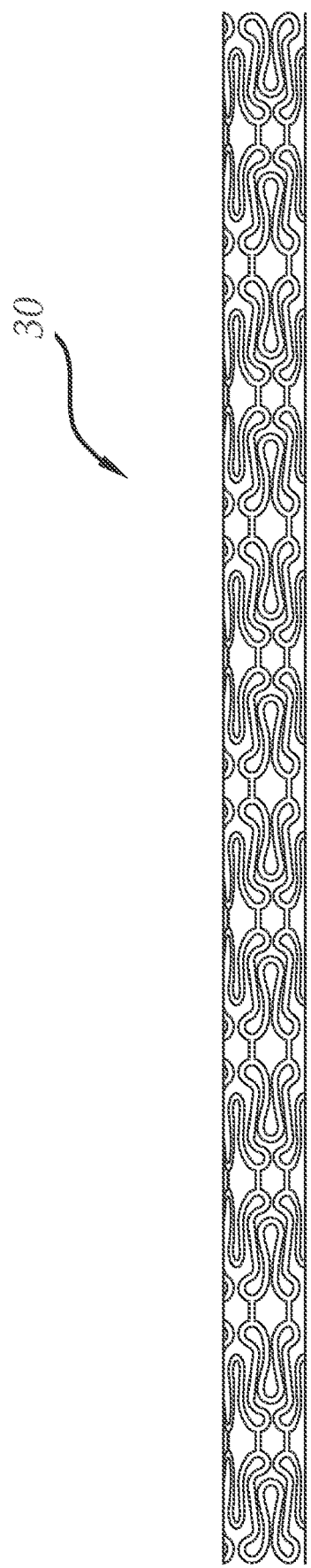
FIG. 3C is a front view of the stent embodiment of FIG. 3A in a collapsed configuration.

FIGS. 3A-C illustrate stent 30 that has the same repeating stent elements $R_1$-$R_4$ and $U_1$-$U_2$ as stent 10; however, stent 30 differs from stent 10 with respect to the connectors between the stent cells 12 and 14. Stent 30 includes straight connectors $C_3$, which connect stent element $R_1$ to stent element $R_3$ and connect stent element $R_2$ to stent element $R_4$ at about the second radius portion $r_2$. In other embodiments, the connector $C_3$ connects only stent elements $R_1$ and $R_3$ or $R_2$ and $R_4$ to provide a more flexible architecture, for example such that there are three connectors $C_3$ along a given circumferential axis rather than the six connectors $C_3$ in stent 30. In one embodiment, the width of connectors $C_3$ are in the range of about 0.0050 inch to about 0.0100 inch, for example about 0.0075 inch. It should be appreciated that the widths and/or lengths of the connectors $C_3$ could vary along one or more circumferential axes and/or alone one or more longitudinal axes, depending on the desired characteristics. For example, the width may be increased for a more rigid stent and decreased for a more flexible stent.

FIG. 3B is a top view of stent 30. In one embodiment, stent 30 is produced from a metal or polymer tube that is laser machined to form the stent architecture.

FIG. 3C illustrates stent 30 in its collapsed configuration. Due to the inventive arrangement of stent elements $R_1$-$R_4$ and $U_1$-$U_2$, the various shapes and curves of the stent cells fit together in a coordinated fashion, thereby providing a very small profile and facilitating collapse for in the case of a balloon expandable stent, crimping) of the stent to a collapsed configuration. It is noted that the collapsed configuration of stents 10 and 20, although not shown herein, appear very similar to the collapsed configuration of stent 30 with respect to the stent elements $R_1$-$R_4$ and $U_1$-$U_2$.

Figure 4A:
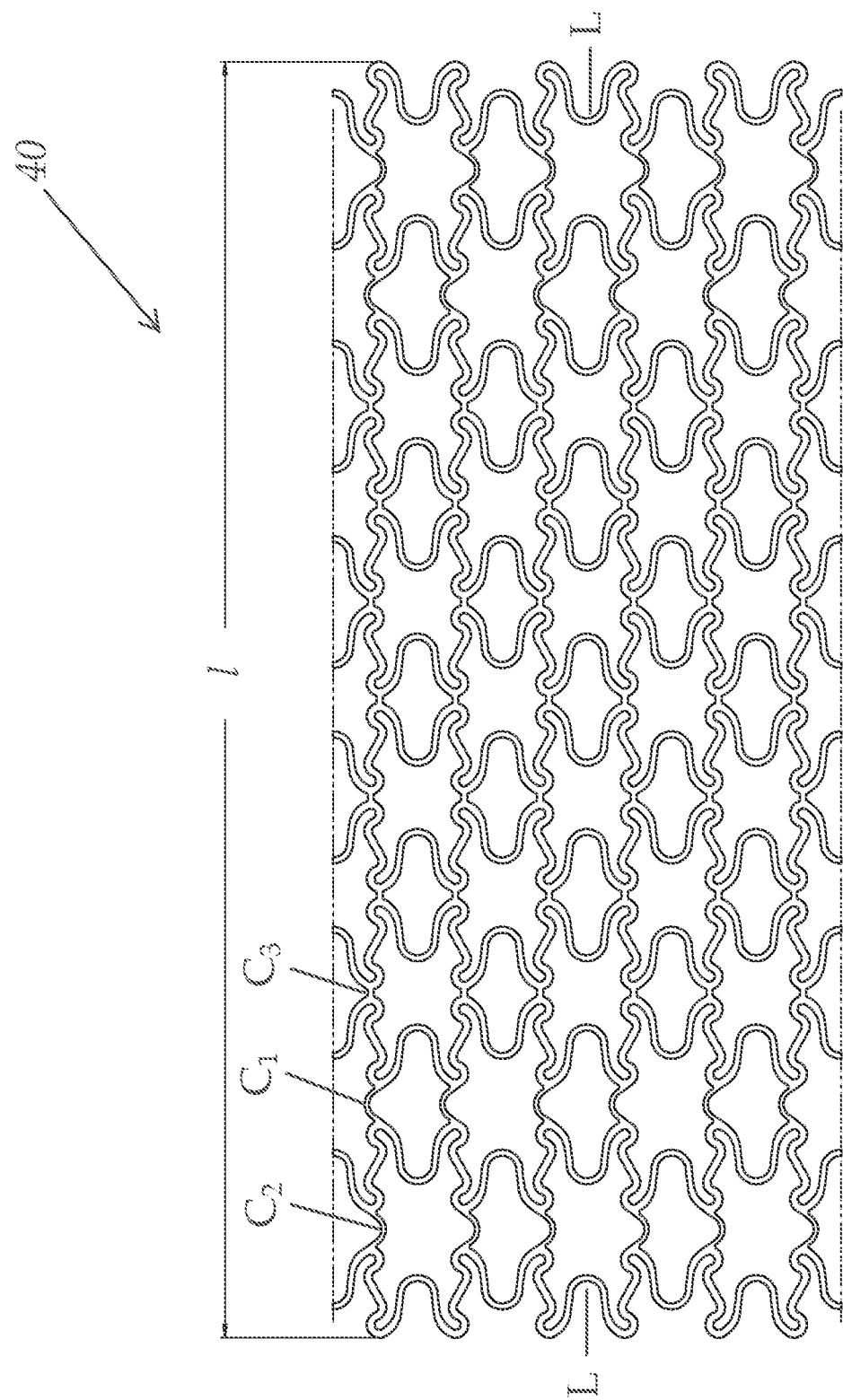
FIG. 4A is a flat view of a stent embodiment in an expanded configuration.
Figure 4B:
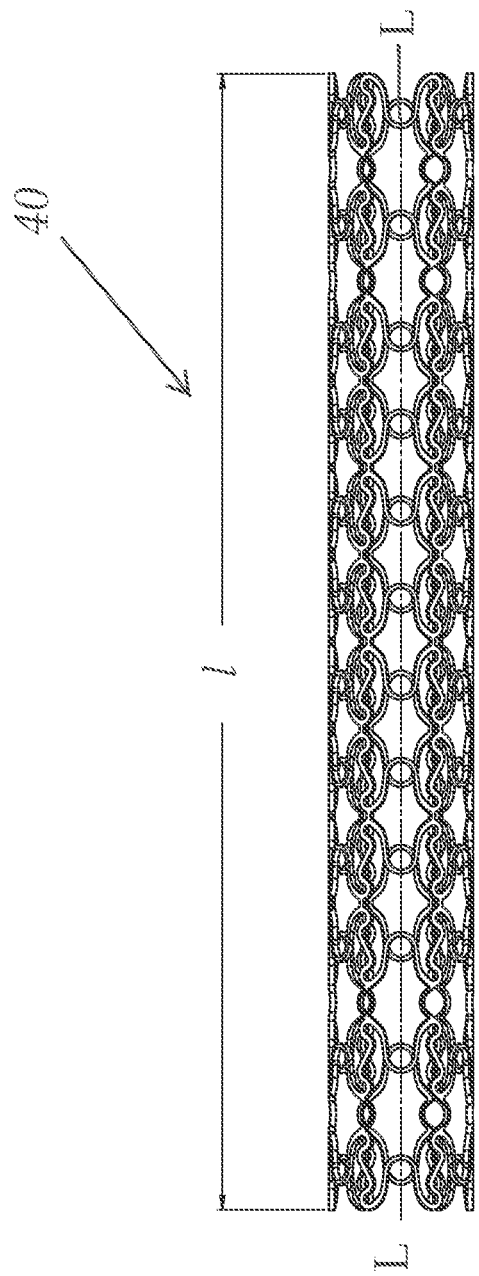
FIG. 4B is a top view of the stent embodiment of FIG. 4A in an as-cut configuration.
Figure 4C:
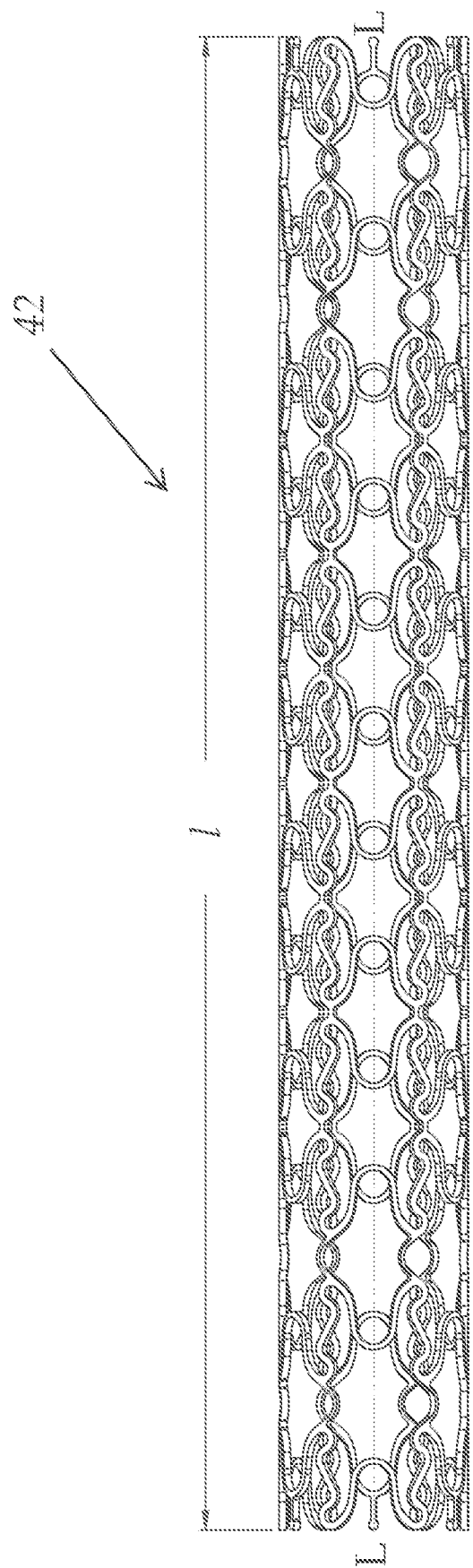
FIG. 4C is a top view of a stent embodiment in an as-cut configuration.

FIGS. 4A-B illustrate stent 40 with the same repeating stent elements $R_1$-$R_4$ and $U_1$-$U_2$ as stent 10; however, stent 40 utilizes connectors $C_1$, $C_2$ and $C_3$. In particular, the stent cells along the two end circumferential axes at both ends of the stent 40 are in the same configuration as stent 20, and the stent cells along the circumferential axes therebetween are connected by connectors $C_3$. FIG. 4B is a top view of stent 40. In one embodiment, stent 40 is produced from a metal or polymer tube that is laser machined to form the stent architecture. FIG. 4C is a top view of stent 42, which is the stent architecture of stent 40 with the addition of receiving members extending from each of the opposing ends of the stent 40, as described above in connection with FIGS. 2A-B.

Figure 5A:
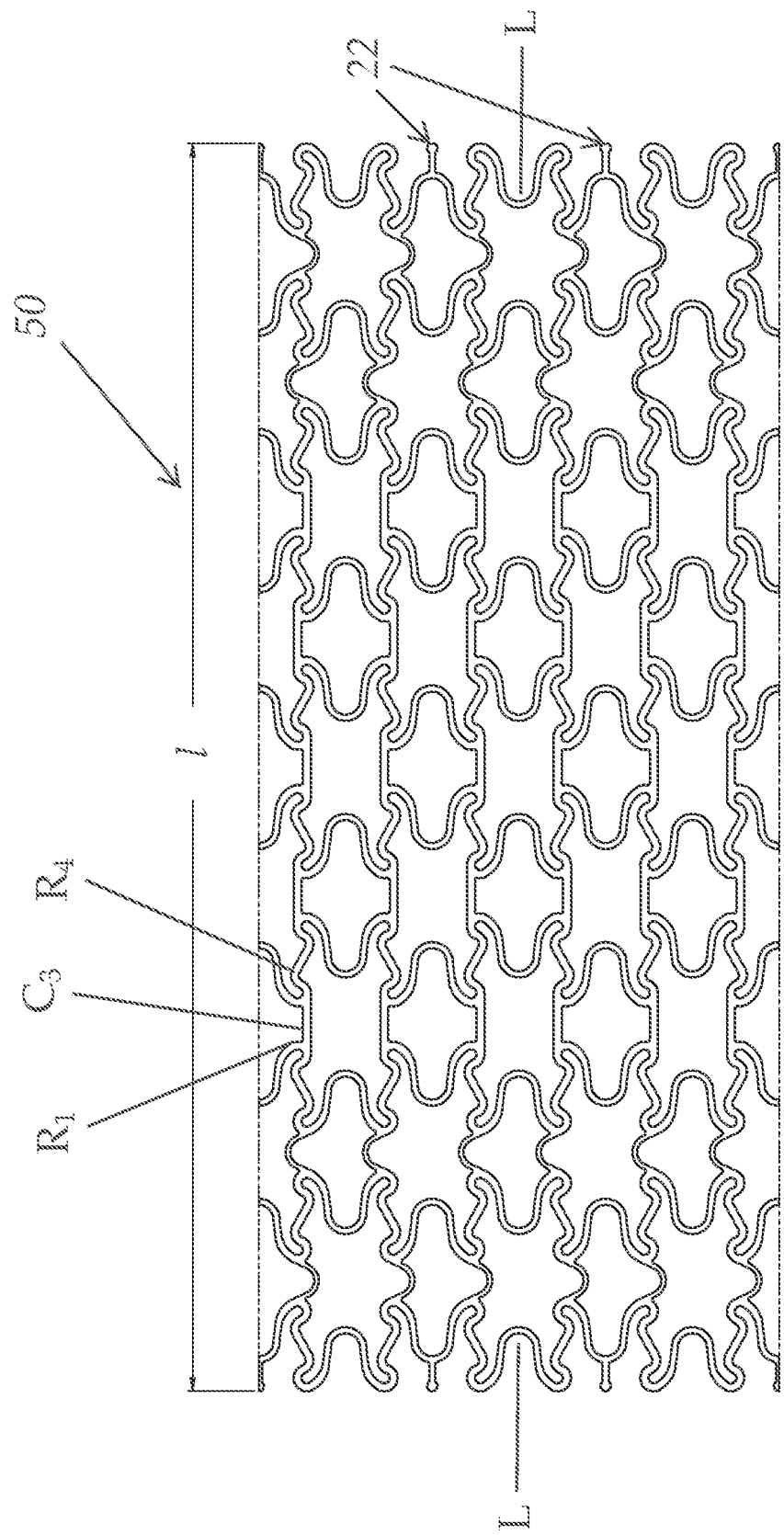
FIG. 5A is a flat view of a stent embodiment in an expanded configuration.
Figure 5C:
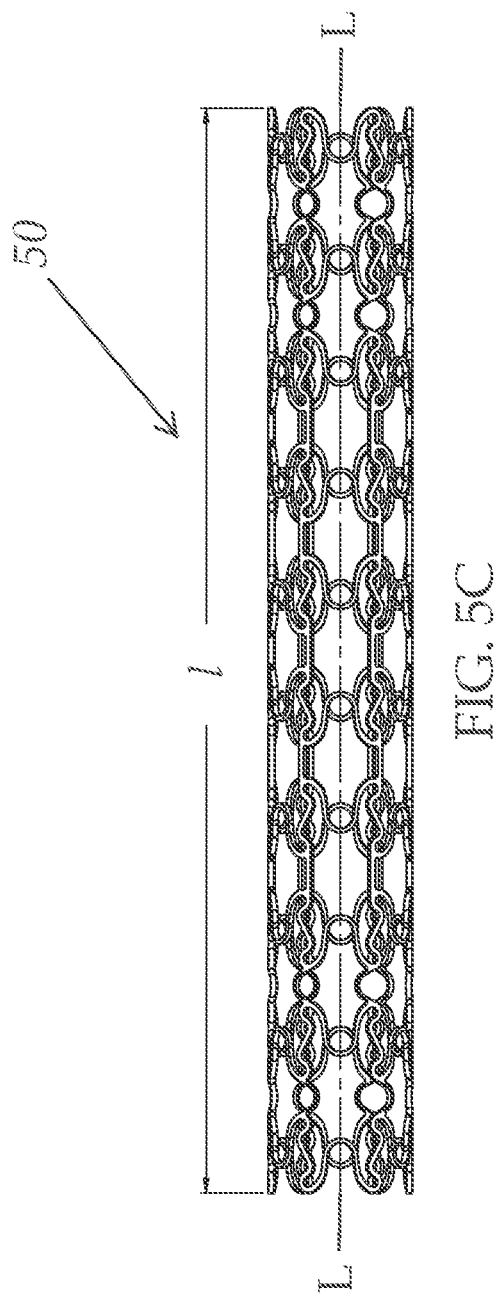
FIG. 5C is a top view of a stent embodiment in an as-cut configuration.

FIG. 5A illustrates stent 50, which is similar to stent 40, but instead of the connectors $C_3$ being attached at about the second radius portion $r_2$ of stent elements $R_1$-$R_4$, they are attached at about the third radius portion $r_3$. Also, stent 50 includes receiving members 22 extending from each of the opposing ends of the stent 50, as described above in connection with FIGS. 2A-B. FIG. 5B is a top view of stent 50. In one embodiment, stent 50 is produced from a metal or polymer tube that is laser machined to form the stent architecture. FIG. 5C is a top view of stent 52, which is the stent architecture of stent 50 without the receiving members extending from the opposing ends.

FIGS. 6A-6D illustrates stent 60 with a stent architecture having stent elements different from the of stents 10, 20, 30, 40 and 50 shown in FIGS. 1-5. That is instead of R-shaped and U-shaped stent elements, stent 60 includes v-shaped stent element $v_1$-$v_4$, indicated in the drawings as $v_1$-$v_4$, each of which include a first leg portion parallel to the longitudinal axis L, a peak portion, and a second leg portion angled with respect to the longitudinal axis, and V-shaped stent elements $V_1$-$V_2$. Beginning from the top left side of FIG. 6A, a repeating series of stent elements is shown along as first side 66 of the stent cells 62 and 64. The stent elements $v_1$, $v_2$, $v_3$, $v_4$ are similar in shape but are or oriented differently from one another with respect to a circumferential axis and/or a longitudinal axis. The stent elements $V_1$ and $V_2$ are facing in opposite directions with respect to a circumferential axis L. The same repeating series of stent elements (arranged identically with respect to the circumferential axis $A_1$ and longitudinal axis L) proceeds along a second side 68 of the stent cells 62 and 64, but is offset such that the sequence begins with stent element $v_3$ which is directly adjacent $v_1$ of the series along the first side 66. Thus beginning from the top of FIG. 6A along second side 68, the series of stent element is $v_3$, $v_4$, $V_2$, $v_1$, $v_2$, $V_1$, $v_3$, etc. The first side 66 is connected to the second side 68 via connectors $C_3$. Stent element $v_1$ of the first side 66 is connected to stent element $v_3$ of the second side 68 at each instance along the circumferential axis $A_1$ in which stent elements $v_1$ and $v_3$ are adjacent one another. The connectors $C_3$ are attached to the stent elements $v_1$ and $v_3$ at about a peak portion thereof to align with the first leg portion thereof that is parallel to the longitudinal axis L. In stent 60, the connectors $C_3$ have a width equal to the width of the first leg portions of $v_1$ and $v_3$. The side of stent element adjacent to the second side 68 (toward the middle of the stent 60) are connected to the second side 68 in the same manner, that is stent elements $v_1$ and $v_3$ are connected by connectors $C_3$ at location where the peak portion of $v_1$ is adjacent the peak portion of $v_3$. This pattern continues down the length of the stent 60.

It is noted that stent elements $v_2$ and $v_4$ are not connected to one another by a connector when the peak portions thereof are adjacent one another. In other embodiments, these peak portions are connected by a connector, for example one of the connectors $C_1$, $C_2$ or $C_3$. In yet other embodiments, instead of stent 60 including only connectors $C_3$, one or both of connectors $C_1$ and $C_2$ could be utilized (see, e.g. FIGS. 9A-C). In still other embodiments, the connectors could connect $V_1$ and $V_2$ instead of, or in addition to connecting $v_1$ and $v_3$ and/or $v_2$ and $v_4$. For example, in one embodiment, a straight connector could connect $V_1$ and $V_2$ at locations where the peak portions thereof are facing away from each other (i.e., across stent cell 62). It is also noted that, in the embodiment shown, the peak portions of the stent elements $v_1$-$v_4$ are longitudinally spaced a distance $D_3$ from the peak portions of $V_1$ and $V_2$, which in one embodiment at a diameter of about 6 mm is in the range from about 0.010 inch to about 0.020 inch, for example about 0.015 inch. In other embodiments, the peak portions are circumferentially aligned.

FIG. 6B is a top view of stent 60. In one embodiment, stent 60 is produced from a metal or polymer tube that is laser machined to form the stent architecture. In one embodiment, stent 60 has a diameter of about 6 mm and a thickness of about 0.0085 inch post electro-polishing. In an embodiment in which stent 60 is covered by one or more graft layers, stent 60 can be expanded to a larger diameter for covering with the graft layer(s), can be covered with the graft layer(s) at the as-cut diameter, or can be crimped to a smaller diameter for covering with the graft layer(s), following post processing steps such as, for example, electro-polishing. The foregoing embodiments are equally applicable to each of the stent architectures described herein.

Figure 6A:
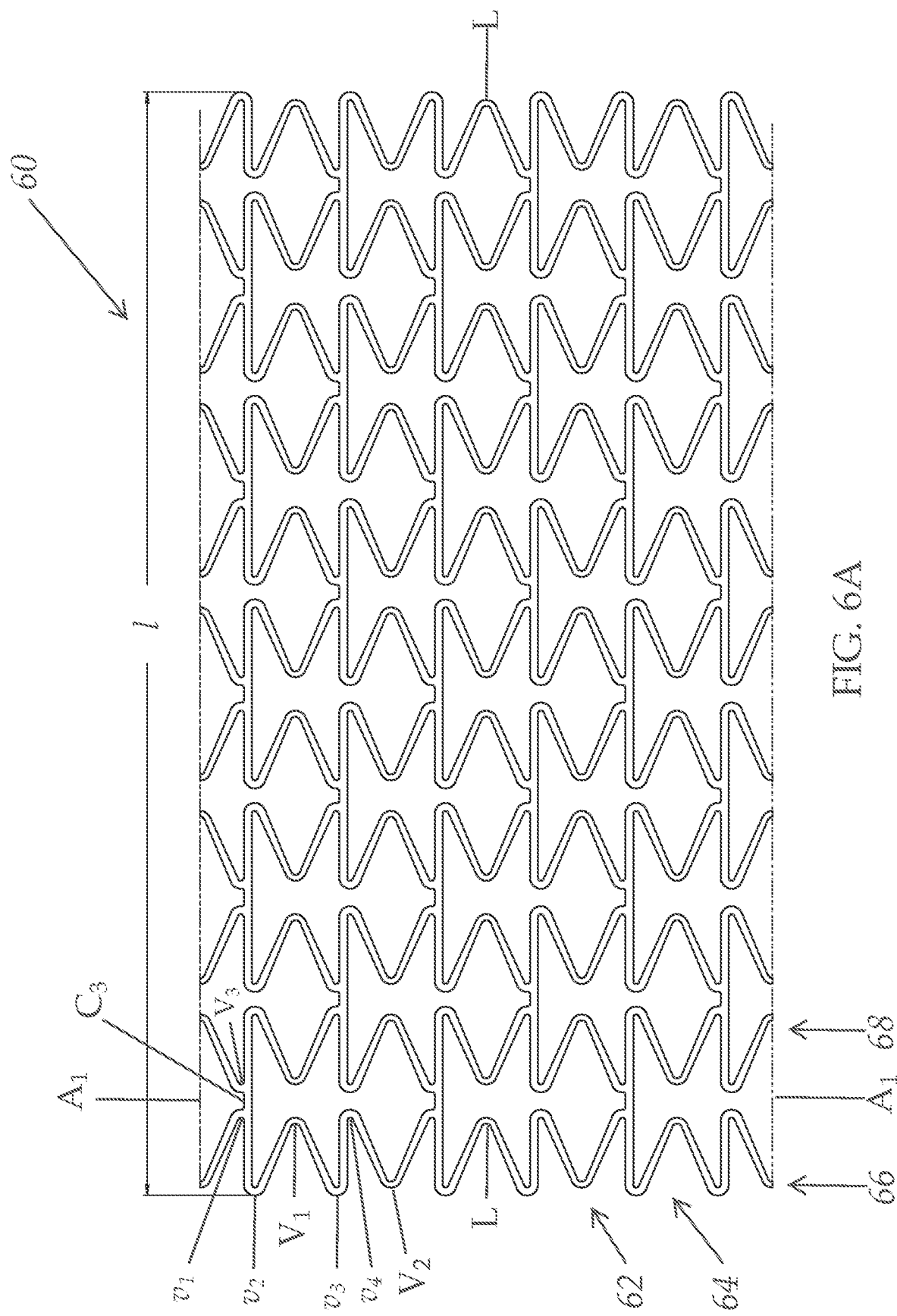
FIG. 6A is a flat view of a stent embodiment in an expanded configuration.
Figure 6D:
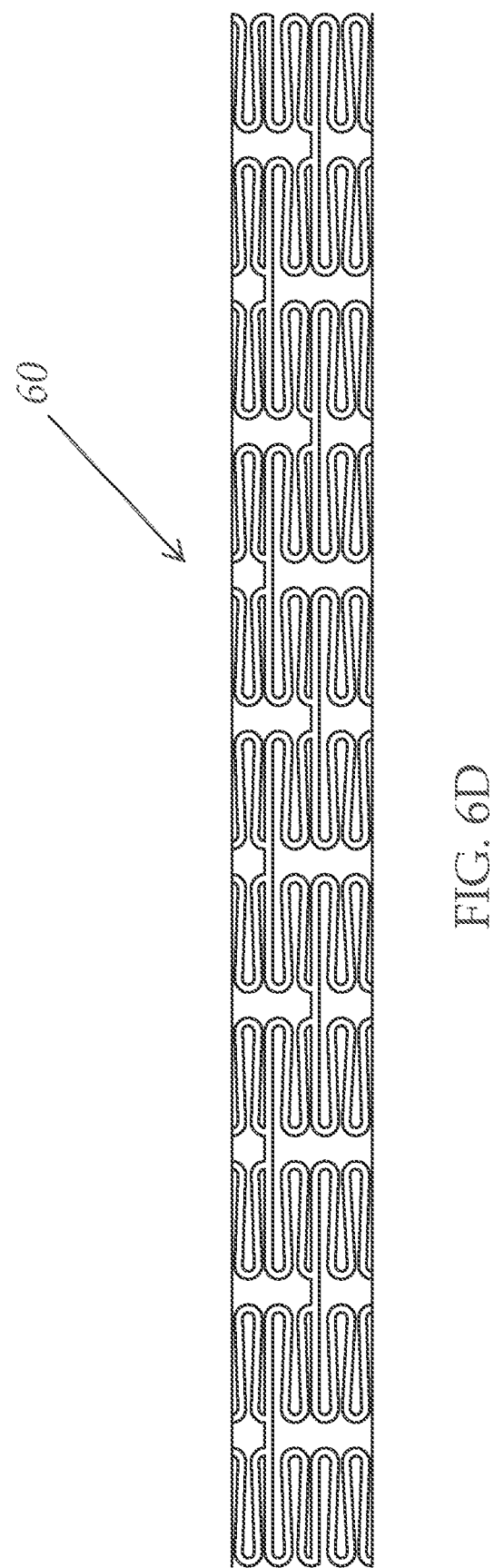
FIG. 6D is a front view of the stent embodiment of FIG. 6A in a collapsed configuration.

In the embodiment of FIGS. 6A-D, the width of selected portions of the stent elements $v_1$-$v_4$ is tapered to a narrowed width for stent elements $V_1$-$V_2$ to promote uniform expansion of the stent. As discussed above, such uniform expansion is preferable, for example, for stents covered by graft material to avoid tearing or deformation of the graft material upon deployment. In other embodiments, the thickness of selected stent elements is reduced instead of, or in conjunction with, the tapered and narrowed of the widths thereof. In FIG. 6C, widths $w_6$-$w_9$ are shown at different locations on the strut cells. Width $w_6$ is at the beginning of second leg portion of stent element $v_2$, width $w_7$ is along the length of first leg portion of stent elements $v_1$ and $v_2$, width $w_8$ is at a section of stent element $V_1$, and width $w_9$ is at a section of connector $C_3$. In the embodiment shown, the widths of $w_6$, $w_7$, and $w_9$ are the same, and the width of $w_8$ is less than the widths of $w_6$, $w_7$, and $w_9$. It is noted that the first leg portions and peak portions of stent elements $v_1$-$v_4$ have the same width along the length thereof (i.e., $w_6$, $w_7$), but second leg portions of each of stent elements $v_1$-$v_4$ taper from width $w_6$ to width $w_8$ along the length thereof. In one embodiment, which could be used in a vessel diameter of about 5 mm to about 15 mm, the widths of $w_6$, $w_7$ and $w_9$ are in the range from about 0.0070 inch to about 0.0120 inch, for example about 0.0095 inch, and the width at w8 is in the range from about 0.0040 inch to about 0.0090 inch, for example about 0.0065 inch. For smaller or larger vessels, dimensions can be accordingly smaller or larger.

Figure 7A:
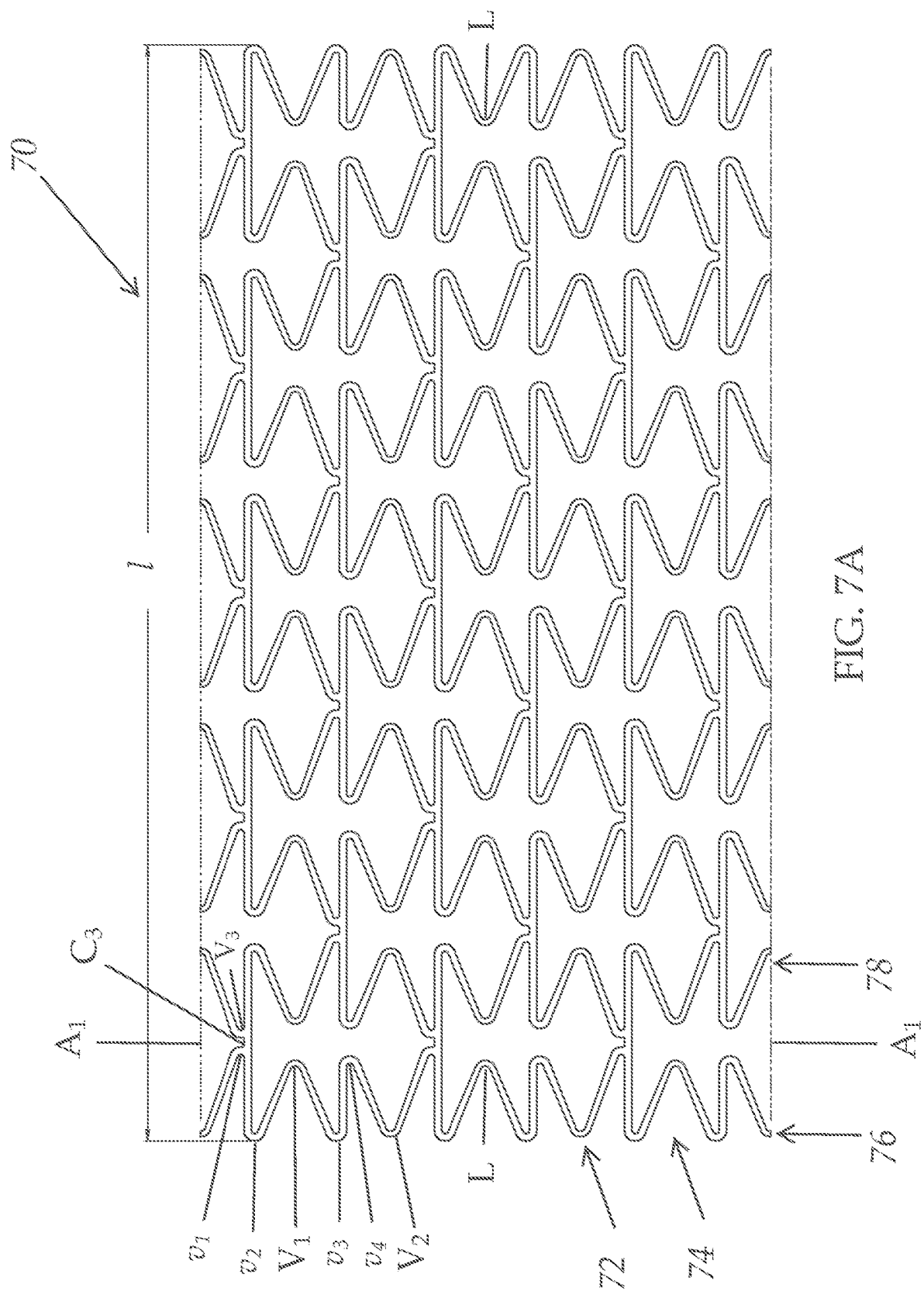
FIG. 7A is a flat view of a stent embodiment in an expanded configuration.

FIGS. 7A-C illustrates stent 70 with a stent architecture including v-shaped stent elements $v_1$-$v_4$, indicated in the drawings as $v_1$-$v_4$, each of which include a first leg portion parallel to the longitudinal axis L, a peak portion, and a second leg portion angled with respect to the longitudinal axis, and V-shaped stent elements $V_1$-$V_2$. Beginning from the top left side of FIG. 7A, a repeating series of stent elements is shown along a first side 76 of the stent cells 72 and 74. The stent elements $v_1$, $v_2$, $v_3$, $v_4$ are similar in shape but are oriented differently from one another with respect to a circumferential axis and/or a longitudinal axis. The stent elements $V_1$ and $V_2$ are facing in opposite directions with respect to a circumferential axis L. The same repeating series of stent elements (arranged identically with respect to the circumferential axis $A_1$ and longitudinal axis L) proceeds along a second side 78 of the stent cells 72 and 74, but is offset such that the sequence begins with stent element $v_3$ Which is directly adjacent $v_1$ of the series along the first side 76. Thus, beginning from the top of FIG. 7A along second side 78, the series of stent elements is $v_3$, $v_4$, $V_2$, $v_1$, $v_2$, $V_1$, $v_3$, etc. The first side 76 is connected to the second side 78 via connectors $C_3$. Stent element $v_1$ of the first side 76 is connected to stent element $v_3$ of the second side 78 at each instance along the circumferential axis $A_1$ in which stent elements $v_1$ and $v_3$ are adjacent one another. The connectors $C_3$ are attached to the stent elements $v_1$ and $v_3$ at about a peak portion thereof to align with the first leg portion thereof that is parallel to the longitudinal axis L. In stent 70, the connectors $C_3$ have a width equal to the width of the first leg portions of $v_1$ and $v_3$. The side of stent elements adjacent to the second side 78 (toward the middle of the stent 70) are connected to the second side 78 in the same manner, that is stent elements $v_1$ and $v_3$ are connected by connectors $C_3$ at locations where the peak portion of $v_1$ is adjacent the peak portion of $v_3$. This pattern continues down the length of the stent 70.

It is noted that stent elements $v_2$ and $v_4$ are not connected to one another by a connector when the peak portions thereof are adjacent one another. In other embodiments, these peak portions are connected by a connector. In yet other embodiments, instead of stent 70 including only connectors $C_3$, other connector types could be utilized. In still other embodiments, the connectors could connect $V_1$ and $V_2$ instead of, or in addition to connecting $v_1$ and $v_3$ and/or $v_2$ and $v_4$. For example, in one embodiment, a straight connector could connect $V_1$ and $V_2$ at locations where the peak portions thereof are facing away from each other (i.e. across stent cell 72). In one embodiment, the peaks connected by one or more of the connectors $C_3$ could be touching, such that the effective length of one or more of the connectors $C_3$ is zero.

Figure 7D:
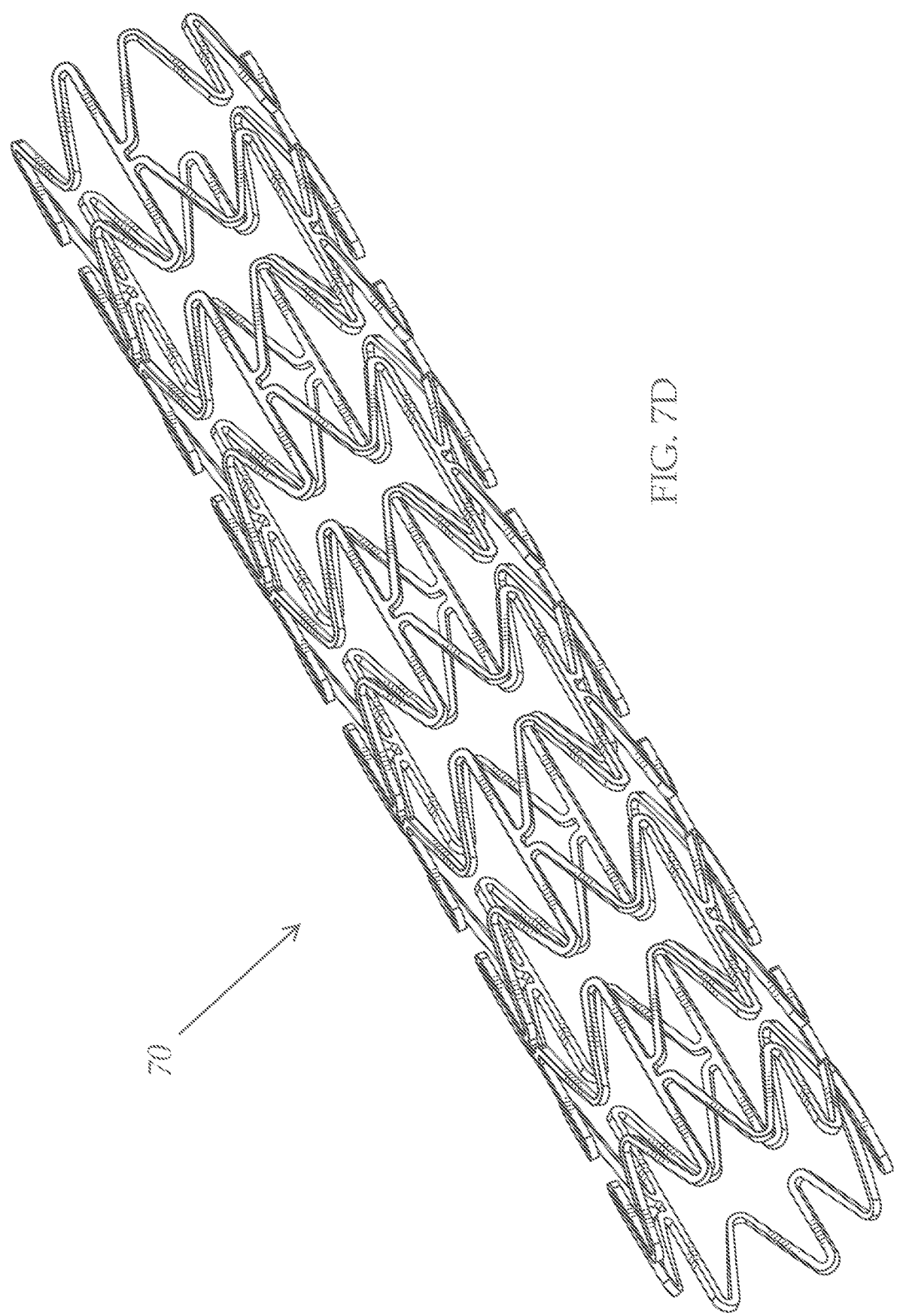
FIG. 7D is an isometric view of the stent embodiment of FIG. 7A in an as-cut configuration.

FIG. 7B is a top view of stent 70. FIG. 7D is an isometric view of stent 70. In one embodiment, stent 70 is produced from a metal or polymer tube that is laser machined to form the stent architecture. In one embodiment, stent 70 has a diameter of about 6 mm and a thickness of about 0.0085 inch post electro-polishing. In an embodiment in which stent 70 is covered by one or more graft layers, stent 70 can be expanded to a larger diameter for covering with the graft layer(s), can be covered with the graft layer(s) at the as-cut diameter, or can be crimped to a smaller diameter for covering with the graft layer(s), following post processing steps such as, for example, electro-polishing.

In the embodiment of FIGS. 7A-C, the width of selected portions of the stent elements $v_1$-$v_4$ is tapered to a narrowed width for stent elements $V_1$-$V_2$ to promote uniform expansion of the stent. In other embodiments, the thickness of selected stent elements is reduced instead of, or in conjunction with, the tapered and narrowed of the widths thereof. In FIG. 7C, widths $w_6$-$w_9$ are shown at different locations on the strut cells. Width $w_6$ is at the beginning of second leg portion of stent element $v_2$, width $w_7$ is along the length of first leg portion of stent elements $v_1$ and $v_2$, width $w_8$ is at a section of stent element $V_1$, and width $w_9$ is at a section of connector $C_3$. In the embodiment shown, the widths of $w_6$, $w_7$, and $w_9$ are the same, and the width of $w_8$ is less than the widths of $w_6$, $w_7$, and $w_9$. It is noted that the first leg portions and peak portions of stent elements $v_1$-$v_4$ have the same width along the length thereof (i.e., $w_6$, $w_7$), but second leg portions of each of stent elements $v_1$-$v_4$ taper from width $w_6$ to width $w_8$ along the length thereof. In one embodiment, which could be used in a vessel diameter of about 5 mm to about 15 mm, the widths of $w_6$, $w_7$ and $w_9$ are in the range from about 0.0070 inch to about 0.0120 inch, for example about 0.0095 inch, and the width at w8 is in the range from about 0.0040 inch to about 0.0090 inch, for example about 0.0065 inch. For smaller or larger vessels, dimensions can be accordingly smaller or larger.

In FIG. 7C, the peak portions of the stent elements $v_1$-$v_4$ are shown longitudinally spaced a distance $D_3$ from the peak portions of $V_1$ and $V_2$, which in one embodiment at a diameter of about 6 mm is in the range from about 0.005 inch to about 0.035 inch, for example about 0.018 inch. In other embodiments, the peak portions are circumferentially aligned. Also in FIG. 7C, the peak portions of the stent elements $v_2$ and $v_4$ are shown longitudinally spaced, respectively, a distance $D_4$ from the peak portions of the stent elements $v_3$ and $v_1$, which in one embodiment at a diameter of about 6 mm is in the range from about 0.005 inch to about 0.035 inch, for example about 0.012 inch. The distance $D_4$ provides increased spacing for the unconnected peaks to allow additional room for expansion to better ensure that the unconnected peaks don't come into contact during delivery and/or deployment.

Figure 8A:
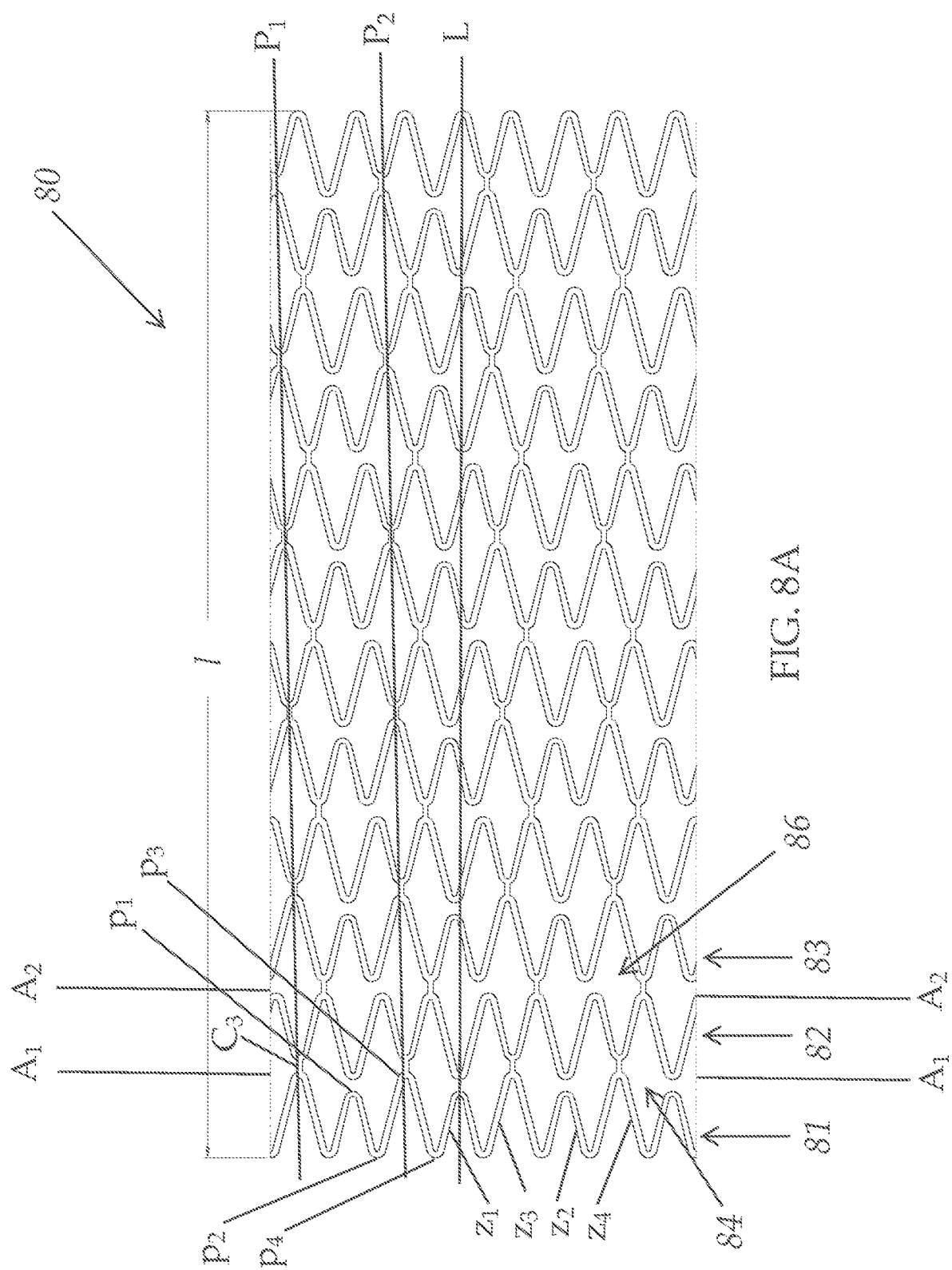
FIG. 8A is a flat view of a stent embodiment in an expanded configuration.
Figure 8B:
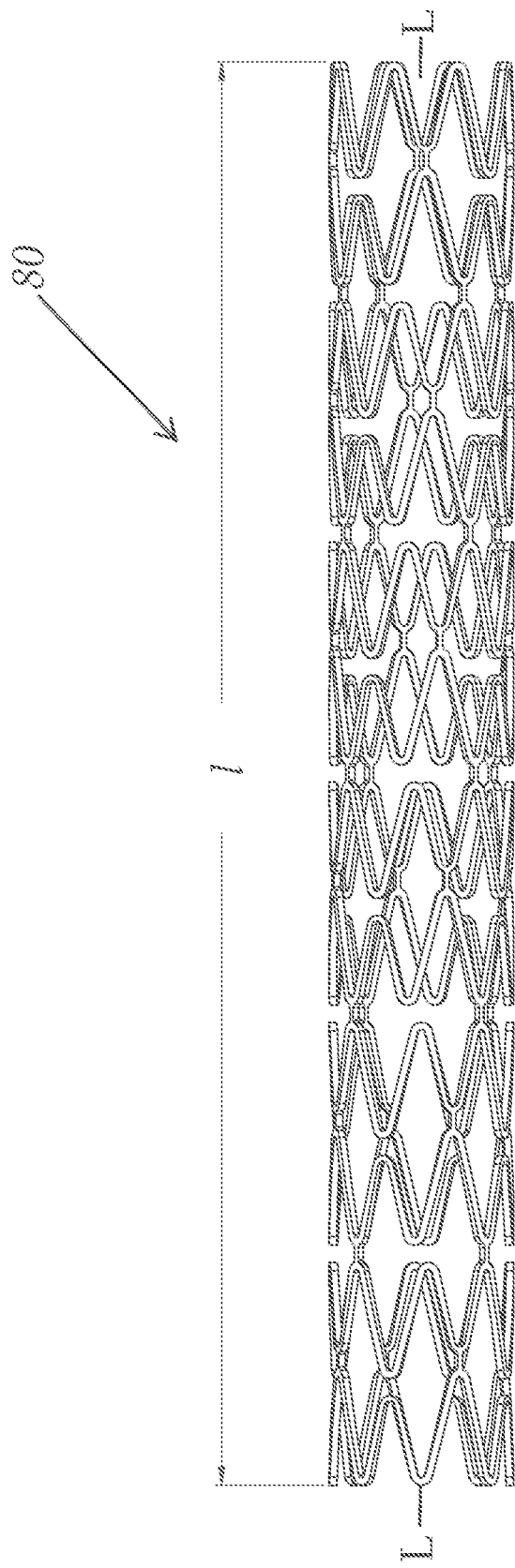
FIG. 8B is a top view of the stent embodiment of FIG. 8A in an as-cut configuration.

FIGS. 8A-B show stent 80 with a stent architecture formed by a series of zig-zag rings formed from stent elements $z_1$-$z_4$ in the form of straight strut members positioned at an angle to the longitudinal axis L and connected together by peak portions $p_1$-$p_4$, where stent element $z_1$ is connected to stent element $z_2$ by peak portion $p_1$, stent element $z_2$ is connected to stent element $z_3$ by peak portion $p_2$, stent element $z_3$ is connected to stew element $z_4$ by peak portion $p_3$, and stew element $z_4$ is connected to stent element $z_1$ by peak portion $p_4$. Adjacent zing-zag rings of repeating stent elements $z_1$-$z_4$ and $p_1$-$p_4$ are connected together by connectors $C_3$ to form stent cells 84 and 86. It is noted that the stent cells have the same shape along a given circumferential axis, and the stent cells along one circumferential axis are different from those of an adjacent circumferential axis. Thus, as shown in FIG. 8A, the stent cells 84 formed through the connection of zig-zag ring 81 to zig-zag ring 82 are the same along circumferential axis $A_1$, but differ from the stent cells 86 along circumferential axis $A_2$ formed through the connection of zig-zag ring 82 to zig-zag ring 83.

The different shapes of stent cells 84 and 86 are produced via an offset of stent elements in the rings along a circumferential axis and by "flipping" the stent elements front one zig-zag ring to the next. Thus, zig-zag ring 82 is the mirror image of zig-zag ring 81 and is offset such that the peak portion $p_3$ of zig-zag ring 81 is connected to the peak portion $p_1$ of zig-zag ring 82, and zig-zag ring 83 is the mirror image of zig-zag ring 82 (i.e., the same orientation as zig-zag ring 81) and is offset such that the peak portion $p_2$ of zig-zag ring 82 is connected to the peak portion $p_4$ of zig-zag ring 83. This pattern repeats down the length of the stent 80.

It is notable that a line drawn through connectors $C_3$ along the longitudinal axis L is slightly angled with respect thereto as illustrated by path $P_1$ and path $P_2$. In one embodiment, the width of stent elements $z_1$ and $z_2$ taper in a direction toward peak portion $p_1$, which has a relatively smaller width, while the width of stent elements $z_3$ and $z_4$ is constant along the length thereof and is the same as the width of peak portions $p_2$, $p_3$, and $p_4$. In one embodiment, the width of stent elements $z_3$, $z_4$ and peak portions $p_2$, $p_3$, and $p_4$ is in the range from about 0.0050 inch to about 0.0100 inch, for example about 0.0075 inch, and the width of peak portion $p_1$ is in the range from about 0.0040 inch to about 0.0070 inch, for example about 0.0055 inch. In one embodiment, the width of connectors $C_3$ is the same as the width of peak portion $p_1$. For smaller or larger vessels, dimensions can be accordingly smaller or larger.

FIG. 8B is a top view of stent 80. In one embodiment, stent 80 is produced from a metal or polymer tithe that is laser machined to form the stent architecture.

Figure 9A:
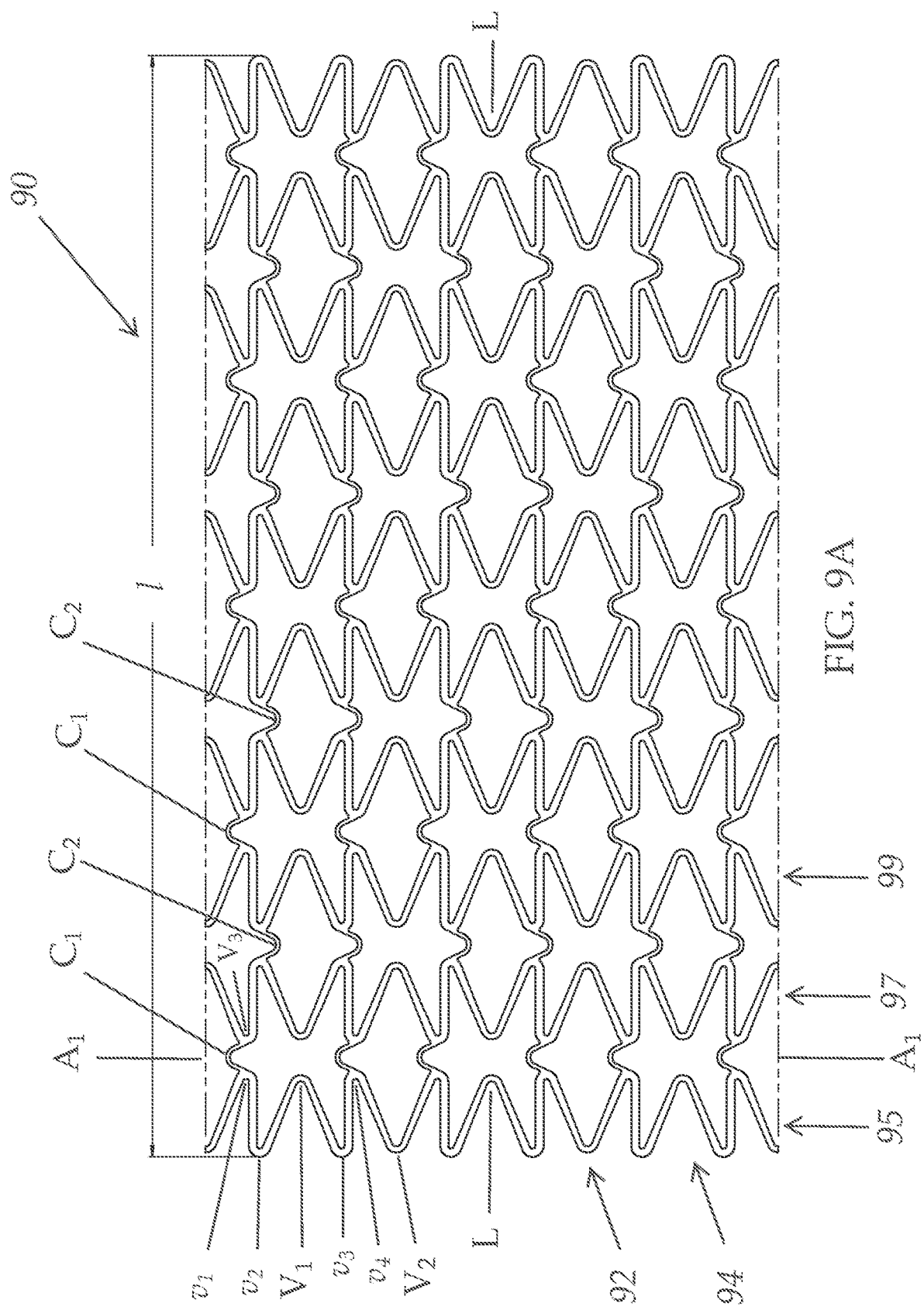
FIG. 9A is a flat view of a stent embodiment in an expanded configuration.
Figure 9B:
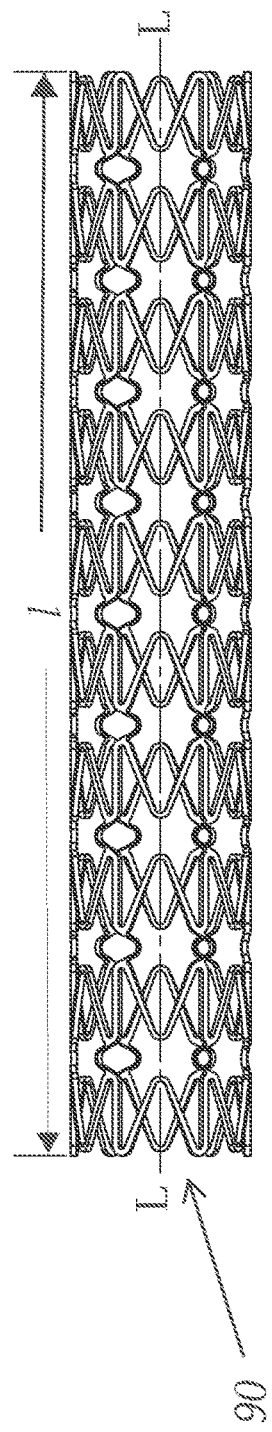
FIG. 9B is a top view of the stent embodiment of FIG. 9A in an as-cut configuration.
Figure 9C:
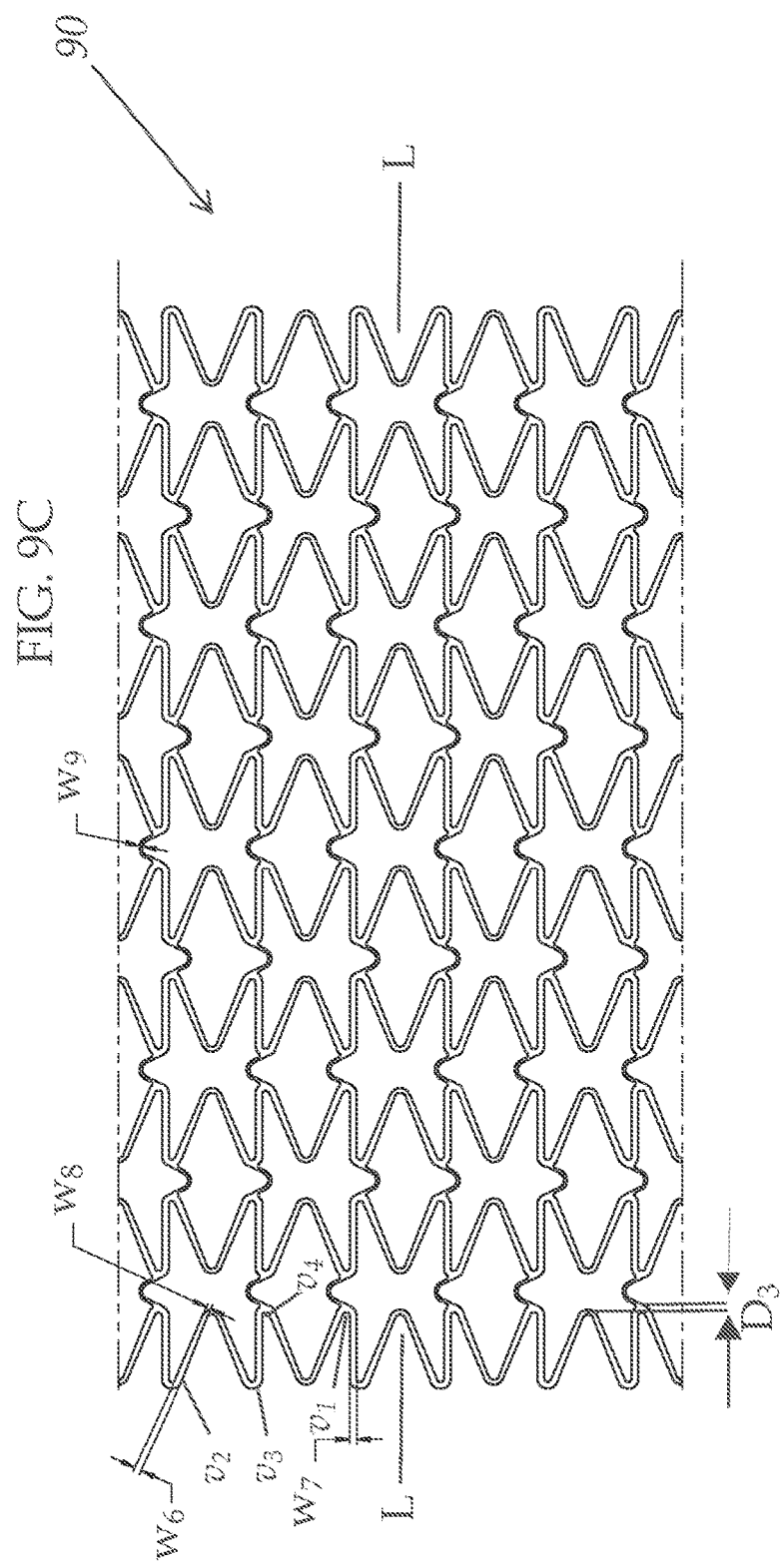
FIG. 9C is a flat view of the stent embodiment of FIG. 9A indicating various dimensions.

FIGS. 9A-C illustrates stent 90 with the stent architecture of stent 60, but with connectors $C_1$ and $C_2$ rather than connectors $C_3$. As with stent 60, stent 90 includes v-shaped stent elements $v_1$-$v_4$, indicated in the drawings as $v_1$-$v_4$, each of which include a first leg portion parallel to the longitudinal axis L, a peak portion, and a second leg portion angled with respect to the longitudinal axis, and V-shaped stent elements $V_1$-$V_2$. Beginning from the top left side of FIG. 9A, a repeating series of stent elements is shown along a first side 95 of the stent cells 92 and 94. The stent elements $v_1$, $v_2$, $v_3$, $v_4$ are similar in shape but are oriented differently front one another with respect to a circumferential axis and/or a longitudinal axis. The stent elements $V_1$ and $V_2$ are facing in opposite directions with respect to a circumferential axis L. The same repeating series of stent elements (arranged identically with respect to the circumferential axis $A_1$ and longitudinal axis L) proceeds along a second side 97 of the stent cells 92 and 94, but is offset such that the sequence begins with stent element $v_3$ which is directly adjacent $v_1$ of the series along the first side 96. Thus, beginning from the top of FIG. 9A along second side 97, the series of stent elements is $v_3$, $v_4$, $V_2$, $v_1$, $v_2$, $V_1$, $v_3$, etc. The first side 95 is connected to the second side 97 via connectors $C_1$. The repeating series of stent elements along a third side 99 is the same as that of the first side 95. The third side 99 is connected to the second side 97 via connectors $C_2$.

It is noted that the connectors are the same along the circumferential axes $A_1$ and $A_2$ (either connectors $C_1$ or $C_2$) and the rows of connectors alternate along the length of the stent 90. Stent element $v_1$ of the first side 95 is connected to stent element $v_3$ of the second side 97 at each instance along the circumferential axis $A_1$ in which stent elements $v_1$ and $v_3$ are adjacent one another. The connectors $C_1$ are attached to the stent elements $v_1$ and $v_3$ at about a peak portion thereof to align with the first leg portion thereof that is parallel to the longitudinal axis L. The third side 99 is connected to the second side 97 in the same manner, that is stent elements $v_1$ and $v_3$ are connected by connectors $C_2$ at locations where the peak portion of $v_1$ is adjacent the peak portion of $v_3$. This pattern continues down the length of the stent 90. It is also noted that, in the embodiment shown, the peak portions of the stent elements $v_1$-$v_4$ are longitudinally spaced a distance $D_3$ from the peak portions of $V_1$ and $V_2$, which in one embodiment is in the range from about 0.010 inch to about 0.020 inch, for example about 0.015 inch. In other embodiments, the peak portions are circumferentially aligned.

FIG. 9B is a top view of stent 90. In one embodiment, stent 90 is produced from a metal or polymer tube that is laser machined to form the stent architecture. In one embodiment, stent 90 has a diameter of about 6 mm and a thickness of about 0.0085 inch post electro-polishing. In an embodiment in which stent 90 is covered by one or more graft layers, stent 90 can be expanded to a larger diameter for covering with the graft layer(s), can be covered with the graft layer(s) at the cut diameter, or can be crimped to a smaller diameter for covering with the graft layer(s), following post processing steps such as, for example, electro-polishing.

In the embodiment of FIGS. 9A-C, as in the embodiment of FIGS. 6A-D, the width of selected portions of the stent elements $v_1$-$v_4$ is tapered to a narrowed width for stent elements $V_1$-$V_2$ to promote uniform expansion of the stent. In other embodiments, the thickness of selected stent elements is reduced instead of or in conjunction with, the tapered and narrowed of the widths thereof. In FIG. 9C, widths $w_6$-$w_9$ are shown at different locations on the strut cells. Width $w_6$ is at the beginning of second leg portion of stent element $v_2$, width $w_7$ is along the length of first leg portion of stent elements $v_1$ and $v_2$, width $w_8$ is at a section of stent element $V_1$, and width $w_9$ is at a section of connector $C_1$. In the embodiment shown, the widths of $w_6$ and $w_7$ are the same, the width of $w_8$ is less than the widths of $w_6$ and $w_7$, and the width of $w_9$ is less than the widths of $w_6$, $w_7$, and $w_8$. It is noted that the first leg portions and peak portions of stent elements $v_1$-$v_4$ have the same width along the length thereof (i.e., $w_6$, $w_7$), but second leg portions of each of stent elements $v_1$-$v_4$ taper from width $w_6$ to width $w_8$ along the length thereof. In one embodiment, which could be used in a vessel diameter of about 5 mm to about 15 mm, the widths of $w_6$ and $w_7$ are in the range from about 0.0070 inch to about 0.0120 inch, for example about 0.0095 inch, the width at $w_8$ is in the range from about 0.0040 inch to about 0.0090 inch, for example about 0.0065 inch, and the width at $w_9$ is in the range from about 0.0020 inch to about 0.0060 inch, for example about 0.0040 inch. For smaller or larger vessels, dimensions can be accordingly smaller or larger.

Figure 10A:
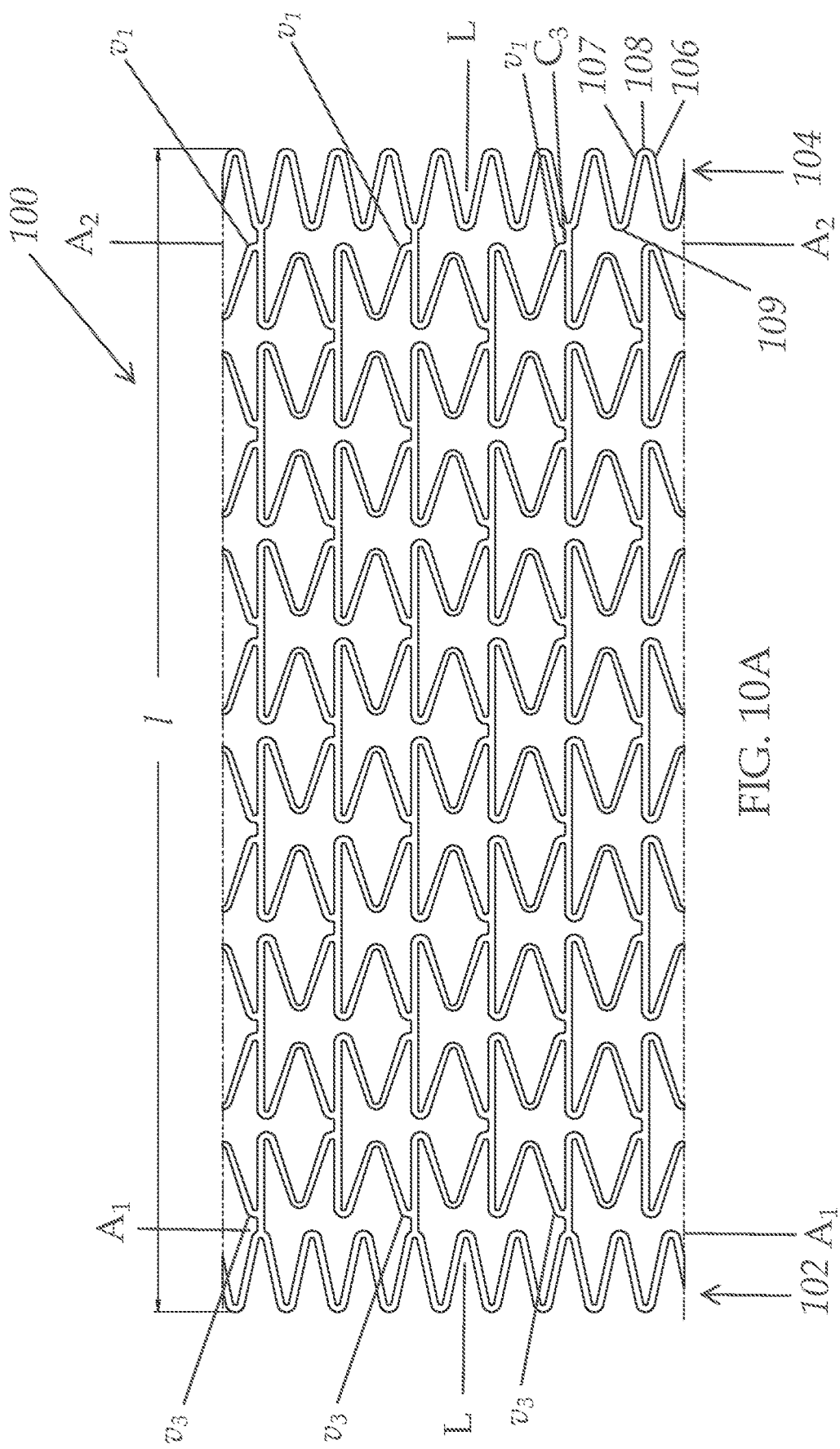
FIG. 10A is a flat view of a stent embodiment in an expanded configuration.
Figure 10B:
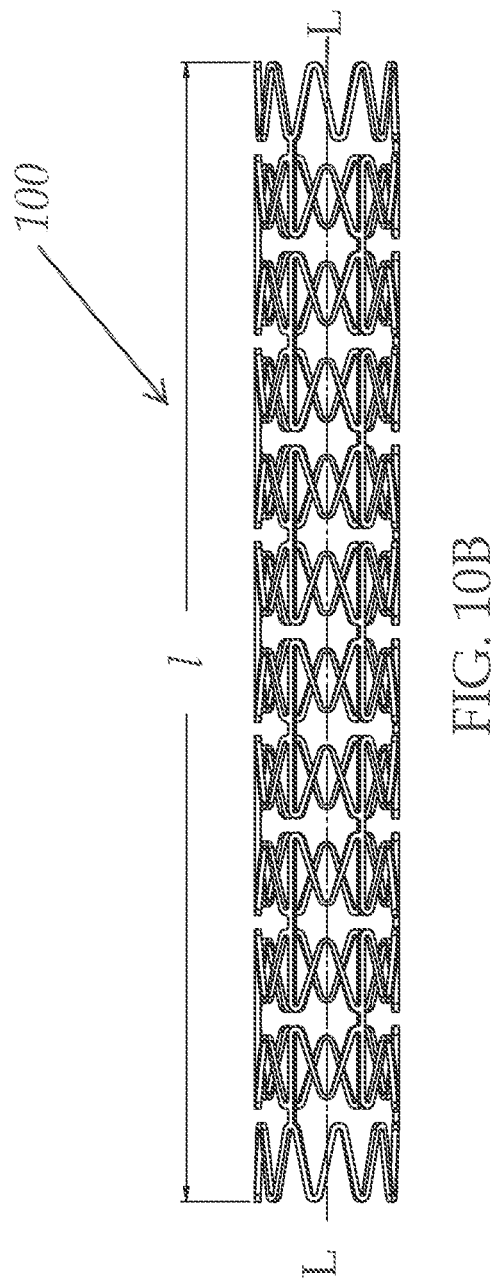
FIG. 10B is a top view of the stent embodiment of FIG. 10A in an as-cut configuration.

FIGS. 10A-B show stent 100, which is a variation of stent 60, having essentially the same stent architecture with the addition of zig-zag ring rings 102 and 104 at opposing proximal and distal ends. The zig-zag rings are formed from stent elements 106, 107 in the form of straight strut members positioned at an angle to the longitudinal axis L and connected together by peak portions 108 and 109. The zig-zag ring 102 is connected to the stent cells at stent element $v_3$ in three locations along circumferential axis $A_1$, and zig-zag ring 104 is connected to the gent cells at stent element $v_1$ in three locations along circumferential axis $A_2$. In other embodiments, the zig-zag rings 102 and 104 could be connected at other locations along the stent cells.

FIG. 10B is a top view of stent 100. In one embodiment, stent 100 is produced from a metal or polymer tube that is laser machined to form the stent architecture.

FIGS. 11A-B illustrate stout 110 that has the same repeating stent elements $R_1$-$R_4$ and $U_1$-$U_2$ as stent 30; however, stent 110 differs from stent 30 with respect to the connectors. Whereas stent 30 includes straight connectors $C_3$, which connect stent element $R_1$ to stent element $R_3$ and connect stent element $R_2$ to stent element $R_4$ at about the second radius portion $r_2$, stent 110 includes straight connectors $C_4$ that connect stent element $U_1$ to stent element $U_2$ when stent elements $U_1$ and $U_2$ on adjacent sides/series, such as sides/series 112 and 114, face toward one another. In another embodiment, the straight connectors $C_4$ connect stent element $U_1$ to stent element $U_2$ when stent elements $U_1$ and $U_2$ on adjacent sides/series, such as sides/series 112 and 114, face away from one another. In yet another embodiment, the straight connectors $C_4$ connect all stent elements $U_1$ to all stent elements $U_2$ on adjacent sides/series (i.e., both those that face toward one another and those that face away from one another). In one embodiment, the width of connectors $C_4$ are in the range of about 0.0050 inch to about 0.0100 inch, for example about 0.007 inch.). In one embodiment, the length of connectors $C_4$ are in the range of about 1.7 mm to about 2.1 mm, for example about 1.9 mm. It should be appreciated that the widths and/or lengths of the connectors $C_4$ could vary along one or more circumferential axes and/or along one or more longitudinal axes, depending on the desired characteristics. For example, the width may be increased for a more rigid stent and decreased for a more flexible stent. It should also be appreciated that the width of individual connectors $C_4$ could vary along the length thereof, for instance narrowing from one or both sides connecting the stent elements $U_1$-$U_2$ toward the middle of the connector $C_4$, or alternatively increasing in width from one or both sides connecting the stent elements $U_1$-$U_2$ toward the middle of the connector $C_4$.

Stent 110 includes receiving members 122 extending from each of the opposing ends of stent 110, the members 122 extending from each stent element $U_2$ (e.g., as shown, six total, three from each side). In one embodiment, the members 122 extend from less than all of the stent elements $U_2$ at one or both ends of stent 110. In one embodiment, the members 122 extend instead from one or more stent elements $U_1$ at one or both ends of stent 110. In one embodiment, the members 122 extend from one or more of both stent elements $U_1$ and $U_2$ at one or both ends of stent 110. Such alternate embodiments for the number and positioning of receiving members 122 are also contemplated with respect to receiving members 22 of FIGS. 2A-B and other stent architectures described herein. The receiving members 122 include a post portion a post portion 124 and an enlarged portion 126 at the end of the member 122 remote from the stent element $U_2$. The enlarged portion 126 includes a bore or opening 128 sized to receive a radiopaque element therein formed from gold, tantalum, platinum, tungsten, and/or other suitable radiopaque materials. In one embodiment, the width of the post portion 124 of the receiving members 122 is about 0.0095 inch, and the diameter of the bore or opening 128 is about 0.0145. The receiving members 122 have a length such that the end thereof generally aligns circumferentially with the outermost end of the stent elements at each opposing end of stent 110. By aligning the outermost ends of the stent elements and receiving members, in an embodiment including one or more graft layers, the graft layer(s) can be in the form of a tube without altering the ends thereof, the receiving members supporting the tubular ends of the graft layer(s) upon collapse and/or expansion of the stent. It is noted that the receiving members of FIGS. 11A-B could be incorporated into any of the other stent architectures described herein.

FIG. 11B is a top view of stent 110. In one embodiment, stent 110 is produced from a metal or polymer tube that is laser machined to form the stent architecture.

While the invention has been described in terms of particular variations and illustrative figures, those of ordinary skill in the art will recognize that the invention is not limited to the variations or figures described. For example, in any of the described stent architectures, the width, length and/or thickness of the stent elements and/or connectors may be varied to enhance desired performance. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An intraluminal prosthesis, comprising: a stent architecture comprising: a plurality of stent cells defined by connected stent rings, each stent ring comprising: a series of stent elements repeating along a circumferential axis, including: R-shaped stent elements having at least four different orientations with respect to the circumferential axis, the R-shaped stent elements having at least a first straight portion, and U-shaped stent elements having at least two different orientations, the U-shaped stent elements connecting adjacent R-shaped stent elements such that the first straight portion of each of the R-shaped stent elements is connected to a U-shaped stent element, the first straight portion of each of the R-shaped stent elements narrowing in width toward the U-shaped stent element.

2. The intraluminal prosthesis according to claim 1, wherein the R-shaped stent elements include at least first, second, third and fourth curved radius portions.

3. The intraluminal prosthesis according to claim 1, wherein the plurality of stent cells includes a first stent cell and a second stent cell different from the first stent cell, the first and second stent cells alternating along the circumferential axis.

4. The intraluminal prosthesis according to claim 1, wherein the R-shaped stent elements include:
a first R-shaped stent element in a first orientation,
a second R-shaped stent element in a second orientation different from the first orientation,
a third R-shaped stent element oriented in a third orientation different from the first and second orientations, and
a fourth R-shaped stent element in a fourth orientation different from the first, second, and third orientations.

5. The intraluminal prosthesis according to claim 4, wherein the U-shaped stent elements include a first U-shaped stent element in a first orientation and a second U-shaped stent element oriented in a second orientation different from the first orientation.

6. The intraluminal prosthesis according to claim 5, wherein:
the first R-shaped stent element is connected to the second U-shaped stent element and the second R-shaped stent element,
the second R-shaped stent element is connected to the first R-shaped stent element and the first U-shaped stent element,
the first U-shaped stent element is connected to the second R-shaped stent element and the third R-shaped stent element,
the third R-shaped stent element is connected to the first U-shaped stent element and the fourth R-shaped stent element, and
the fourth R-shaped stent element is connected to the third R-shaped stent element and the second U-shaped stent element.

7. The intraluminal prosthesis according to claim 5, wherein the stent architecture further comprises a plurality of connectors connecting adjacent series of stent elements, the connectors connecting the first U-shaped stent element in a first series of stent elements to the second U-shaped stent element in a second adjacent series of stent elements.

8. The intraluminal prosthesis according to claim 4, wherein the stent architecture further comprises a plurality of connectors connecting adjacent series of stent elements, the connectors connecting the first R-shaped stent element in a first series of stent elements to the third R-shaped stent element in a second adjacent series of stent elements.

9. The intraluminal prosthesis according to claim 8, wherein the connectors further connect the fourth R-shaped stent element in the first series of stent elements to the second R-shaped stent element in the second adjacent series of stent elements.

* * * * *